(12) United States Patent
Williams

(10) Patent No.: US 9,193,795 B2
(45) Date of Patent: Nov. 24, 2015

(54) METHOD FOR MAKING TARGETED THERAPEUTIC AGENTS

(75) Inventor: Richard B. Williams, South Pasadena, CA (US)

(73) Assignee: PROTEONOVA, INC., Pasadena, CA (US)

( * ) Notice: Subject to any disclaimer, the term of this patent is extended or adjusted under 35 U.S.C. 154(b) by 0 days.

(21) Appl. No.: 13/016,576

(22) Filed: Jan. 28, 2011

(65) Prior Publication Data

US 2011/0212114 A1  Sep. 1, 2011

Related U.S. Application Data

(63) Continuation of application No. 11/813,849, filed as application No. PCT/US2006/000956 on Jan. 12, 2006, now abandoned.

(60) Provisional application No. 60/643,191, filed on Jan. 12, 2005.

(51) Int. Cl.
| | |
|---|---|
| C07K 14/00 | (2006.01) |
| C07K 16/30 | (2006.01) |
| G01N 33/531 | (2006.01) |
| G01N 33/68 | (2006.01) |

(52) U.S. Cl.
CPC ............. *C07K 16/30* (2013.01); *G01N 33/531* (2013.01); *G01N 33/6845* (2013.01); *C07K 14/00* (2013.01); *C07K 2319/30* (2013.01)

(58) Field of Classification Search
CPC ........................................................ C07K 14/00
See application file for complete search history.

(56) References Cited

U.S. PATENT DOCUMENTS

| | | | | |
|---|---|---|---|---|
| 4,882,423 | A * | 11/1989 | Taguchi et al. | 530/380 |
| 5,843,701 | A | 12/1998 | Gold et al. | |
| 5,849,297 | A | 12/1998 | Harrison et al. | |
| 6,306,393 | B1 * | 10/2001 | Goldenberg | 424/141.1 |
| 2003/0059827 | A1 | 3/2003 | Gonzalez et al. | |
| 2004/0167319 | A1 * | 8/2004 | Teeling et al. | 530/388.22 |
| 2004/0265321 | A1 * | 12/2004 | Johnson et al. | 424/178.1 |
| 2007/0160530 | A1 | 7/2007 | Jakobovits et al. | |
| 2007/0253958 | A1 | 11/2007 | Van De Winkel et al. | |
| 2008/0199499 | A1 | 8/2008 | Williams | |
| 2009/0092614 | A1 | 4/2009 | Demarest et al. | |

FOREIGN PATENT DOCUMENTS

| | | |
|---|---|---|
| WO | WO 96/01653 | 1/1996 |
| WO | WO 98/31700 | 7/1998 |
| WO | 01/07657 | 2/2001 |
| WO | 01/90414 | 11/2001 |
| WO | 03/044194 | 5/2003 |
| WO | WO 03/035105 | 5/2003 |
| WO | WO 2004/048413 | 6/2004 |

OTHER PUBLICATIONS

Feng et al., 2002, Complement Component C1q Enhances the Biological Activity of Influenza Virus Hemagglutinin-Specific Antibodies Depending on Their Fine Antigen Specificity and Heavy-Chain Isotype, Journal of Virology, 7693): 1369-1378.*
Reff et al., 1994, Depletion of B cells In Vivo by a Chimeric Mouse Human Monoclonal Antibody to CD20, Blood, 83(2): 435-445.*
Carter, 2001, Improving the Efficacy of Antibody-Based Cancer Therapies, Nature Reviews, 1: 118-129.*
Yefenof et al., 1990, Potentiation of NK Cytotoxicity by Antibody-C3b/iC3b Heteroconjugates, The Journal of Immunology, 144(4): 1538-1543.*
Dempsey et al., 1996, C3d of Complement as a Molecular Adjuvant: Bridging Innate and Acquired Immunity, Science, 271: 348-350.*
Reiter et al., 1989, Killing of Human Tumor Cells by Antibody C3b Conjugates and Human Complement, Targeted Diagn Ther, 2: 119-135.*
Schumaker et al., 1987, Activation of the first component of complement, Ann. Rev. Immunol., 5: 21-42.*
International Search Report and Written Opinion of the International Searching Authority for International Application No. PCT/US06/00956 dated May 11, 2006. [PRONOV.009VPC].
International Preliminary Report on Patentability dated Dec. 23, 2010 [PRONOV.019WO].
Sahu et al., Covalent Attachment of Human Complement C3 to IgG, J. Biol. Chem. 1994, 269:28997-29002.
Lipovsek et al., "In-vitro protein evolution by ribosome display and mRNA display," Journal of Immunological Methods 290: 51-67 (2004).
Takahashi et al., mRNA display: ligand discovery, interaction analysis and beyond, Elsevier: TRENDS in Biochemical Sciences, Mar. 2003, vol. 28 (3), pp. 159-165.
Wang et al., Probing Tat Peptide-TAR RNA Interactions by Psoralen Photo-Cross-Linking, Biochemistry. vol. 40: 6458-6464, 2001.

\* cited by examiner

*Primary Examiner* — Amber D Steele
(74) *Attorney, Agent, or Firm* — Knobbe Martens Olson & Bear, LLP

(57) ABSTRACT

Provided herein are methods and kits for making a targeted therapeutic for treating a disease or condition. The therapeutic agents can be targeted to patient-specific disease markers. In one of these methods, the method includes obtaining a biological sample from a patient having the disease or condition, or who is at risk for developing the disease or condition. In this particular method, the sample includes a population of diseased cells, screening a library comprising proteins linked to their cognate mRNAs to identify mRNA-protein pairs that bind to the diseased cells, isolating one or more proteins from the identified mRNA-protein pairs, and conjugating the isolated protein(s) to a therapeutic agent. Some of the methods further include preparing a library with proteins linked to their cognate mRNAs. In certain of these methods, the preparation of the library includes providing at least two candidate mRNA molecules in which each of the mRNA molecules includes a cross-linker, translating at least two of the candidate mRNA molecules to generate at least one translated protein, and linking at least one of the candidate mRNA molecules to its corresponding translated protein via the cross-linker to form at least one cognate pair.

7 Claims, 16 Drawing Sheets

SEQUENCE LISTING

```
<160> NUMBER OF SEQ ID NOS: 32

<210> SEQ ID NO 1
<211> LENGTH: 13
<212> TYPE: RNA
<213> ORGANISM: Homo sapiens
<220> FEATURE:
<221> NAME/KEY: modified_base
<222> LOCATION: (6)..(6)
<223> OTHER INFORMATION: n= pseudouridine
<220> FEATURE:
<221> NAME/KEY: misc_feature
<222> LOCATION: (6)..(6)
<223> OTHER INFORMATION: n is a, c, g, or u

<400> SEQUENCE: 1
cuagancugg agg                                                      13

<210> SEQ ID NO 2
<211> LENGTH: 13
<212> TYPE: RNA
<213> ORGANISM: Homo sapiens
<220> FEATURE:
<221> NAME/KEY: misc_feature
<222> LOCATION: (2)..(3)
<223> OTHER INFORMATION: bases at positions 2 and 3 are linked by
      psoralen
<220> FEATURE:
<221> NAME/KEY: modified_base
<222> LOCATION: (6)..(6)
<223> OTHER INFORMATION: n= pseudouridine
<220> FEATURE:
<221> NAME/KEY: misc_feature
<222> LOCATION: (6)..(6)
<223> OTHER INFORMATION: n is a, c, g, or u

<400> SEQUENCE: 2
cuagancugg agg                                                      13

<210> SEQ ID NO 3
<211> LENGTH: 23
<212> TYPE: RNA
<213> ORGANISM: Homo sapiens
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (19)..(23)
<223> OTHER INFORMATION: n is a, c, g, or u

<400> SEQUENCE: 3
nnnnnccucc agaucuagnn nnn                                           23
```

```
<210> SEQ ID NO 4
<211> LENGTH: 23
<212> TYPE: RNA
<213> ORGANISM: Homo sapiens
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (16)..(17)
<223> OTHER INFORMATION: bases at 16 and 17 are linked by psoralen
<220> FEATURE:
<221> NAME/KEY: misc_feature
<222> LOCATION: (19)..(23)
<223> OTHER INFORMATION: n is a, c, g, or u

<400> SEQUENCE: 4
nnnnnccucc agaucuagnn nnn                                          23

<210> SEQ ID NO 5
<211> LENGTH: 13
<212> TYPE: RNA
<213> ORGANISM: Homo sapiens
<220> FEATURE:
<221> NAME/KEY: modified_base
<222> LOCATION: (6)..(6)
<223> OTHER INFORMATION: n= pseudouridine
<220> FEATURE:
<221> NAME/KEY: misc_feature
<222> LOCATION: (6)..(6)
<223> OTHER INFORMATION: n is a, c, g, or u

<400> SEQUENCE: 5
cuagancugg agg                                                     13

<210> SEQ ID NO 6
<211> LENGTH: 29
<212> TYPE: DNA
<213> ORGANISM: Homo sapiens
<220> FEATURE:
<221> NAME/KEY: modified_base
<222> LOCATION: (9)..(9)
<223> OTHER INFORMATION: n = pseudouridine
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (29)..(29)
<223> OTHER INFORMATION: Base at position 29 is coupled to puromycin

<400> SEQUENCE: 6
uccugugtnc gauccacaga auucgcacc                                    29

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (2)..(3)
<223> OTHER INFORMATION: bases at 2 and 3 are linked by psoralen
<220> FEATURE:
<221> NAME/KEY: modified_base
<222> LOCATION: (22)..(22)
<223> OTHER INFORMATION: n = pseudouridine
<220> FEATURE:
<221> NAME/KEY: misc_feature
<222> LOCATION: (22)..(22)
<223> OTHER INFORMATION: n is a, c, g, t or u
```

```
<220> FEATURE:
<221> NAME/KEY: misc_feature
<222> LOCATION: (42)..(42)
<223> OTHER INFORMATION: Base at position 42 is coupled to puromycin

<400> SEQUENCE: 7
cuagaycugg agguccugug tncgauccac agaauucgca cc                      42

<210> SEQ ID NO 8
<211> LENGTH: 33
<212> TYPE: DNA
<213> ORGANISM: Homo sapiens

<400> SEQUENCE: 8
gcggauuuag cucaguuggg agagcgccag acu                               33

<210> SEQ ID NO 9
<211> LENGTH: 75
<212> TYPE: DNA
<213> ORGANISM: Homo sapiens
<220> FEATURE:
<221> NAME/KEY: misc_feature
<222> LOCATION: (35)..(36)
<223> OTHER INFORMATION: bases at 35 and 36 are linked by psoralen
<220> FEATURE:
<221> NAME/KEY: modified_base
<222> LOCATION: (39)..(39)
<223> OTHER INFORMATION: n= pseudouridine
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: modified_base
<222> LOCATION: (55)..(55)
<223> OTHER INFORMATION: n= pseudouridine
<220> FEATURE:
<221> NAME/KEY: misc_feature
<222> LOCATION: (55)..(55)
<223> OTHER INFORMATION: n is a, c, g, t or u
<220> FEATURE:
<221> NAME/KEY: misc_feature
<222> LOCATION: (75)..(75)
<223> OTHER INFORMATION: Base at position 75 is coupled to puromycin

<400> SEQUENCE: 9
gcggauuuag cucaguuggg agagcgccag acucuaganc uggagguccu gugtncgauc  60
cacagaauuc gcacc                                                   75

<210> SEQ ID NO 10
<211> LENGTH: 32
<212> TYPE: RNA
<213> ORGANISM: Homo sapiens

<400> SEQUENCE: 10
gcggauuuag cucaguuggg agagcgccag ac                                32

<210> SEQ ID NO 11
<211> LENGTH: 8
<212> TYPE: RNA
<213> ORGANISM: Homo sapiens
<220> FEATURE:
<221> NAME/KEY: modified_base
<222> LOCATION: (1)..(1)
<223> OTHER INFORMATION: n= pseudouridine
<220> FEATURE:
<221> NAME/KEY: misc_feature
<222> LOCATION: (1)..(1)
<223> OTHER INFORMATION: n is a, c, g, or u
<220> FEATURE:
```

<220> FEATURE:
<221> NAME/KEY: modified_base
<222> LOCATION: (7)..(7)
<223> OTHER INFORMATION: n= pseudouridine
<220> FEATURE:
<221> NAME/KEY: misc_feature
<222> LOCATION: (7)..(7)
<223> OTHER INFORMATION: n is a, c, g, or u

<400> SEQUENCE: 11 ncuaacnc                                                                8

<210> SEQ ID NO 12
<211> LENGTH: 35
<212> TYPE: DNA
<213> ORGANISM: Homo sapiens
<220> FEATURE:
<221> NAME/KEY: modified_base
<222> LOCATION: (15)..(15)
<223> OTHER INFORMATION: n= pseudouridine
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (35)..(35)
<223> OTHER INFORMATION: Base at position 35 is coupled to puromycin

<400> SEQUENCE: 12
uggagguccu gugtncgauc cacagaauuc gcacc                                  35

<210> SEQ ID NO 13
<211> LENGTH: 18
<212> TYPE: RNA
<213> ORGANISM: Homo sapiens
<220> FEATURE:
<221> NAME/KEY: modified_base
<222> LOCATION: (4)..(4)
<223> OTHER INFORMATION: n= pseudouridine
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: modified_base
<222> LOCATION: (11)..(11)
<223> OTHER INFORMATION: n= pseudouridine
<220> FEATURE:
<221> NAME/KEY: misc_feature
<222> LOCATION: (11)..(12)
<223> OTHER INFORMATION: n is a, c, g, or u
<220> FEATURE:
<221> NAME/KEY: modified_base
<222> LOCATION: (12)..(12)
<223> OTHER INFORMATION: n= pseudouridine

<400> SEQUENCE: 13
cccnccagag nnagaccc                                                     18

<210> SEQ ID NO 14
<211> LENGTH: 14
<212> TYPE: RNA
<213> ORGANISM: Homo sapiens
<220> FEATURE:
<221> NAME/KEY: modified_base
<222> LOCATION: (7)..(7)
<223> OTHER INFORMATION: n= pseudouridine
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: modified_base

```
<222> LOCATION: (9)..(9)
<223> OTHER INFORMATION: n= pseudouridine
<220> FEATURE:
<221> NAME/KEY: misc_feature
<222> LOCATION: (9)..(9)
<223> OTHER INFORMATION: n is a, c, g, or u

<400> SEQUENCE: 14
ucuaagncng gagg                                                       14

<210> SEQ ID NO 15
<211> LENGTH: 71
<212> TYPE: DNA
<213> ORGANISM: Homo sapiens
<220> FEATURE:
<221> NAME/KEY: modified_base
<222> LOCATION: (32)..(32)
<223> OTHER INFORMATION: n = N3-Methyluridine
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (35)..(36)
<223> OTHER INFORMATION: bases at 35 and 36 are linked by psorlen
<220> FEATURE:
<221> NAME/KEY: modified_base
<222> LOCATION: (39)..(39)
<223> OTHER INFORMATION: n= pseudouridine
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: modified_base
<222> LOCATION: (41)..(41)
<223> OTHER INFORMATION: n= pseudouridine
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (71)..(71)
<223> OTHER INFORMATION: Base at position 72 is coupled to puromycin

<400> SEQUENCE: 15
gcggauuuag cucaguuggg agagcgccag anucuaagnc nggagguccu gugtycgauc     60
cacagaauuc g                                                          71

<210> SEQ ID NO 16
<211> LENGTH: 32
<212> TYPE: RNA
<213> ORGANISM: Homo sapiens

<400> SEQUENCE: 16
gcggauuuag cucaguuggg agagcgccag ac                                   32

<210> SEQ ID NO 17
<211> LENGTH: 8
<212> TYPE: RNA
<213> ORGANISM: Homo sapiens
<220> FEATURE:
<221> NAME/KEY: modified_base
<222> LOCATION: (1)..(1)
<223> OTHER INFORMATION: n= pseudouridine
<220> FEATURE:
<221> NAME/KEY: misc_feature
<222> LOCATION: (1)..(1)
<223> OTHER INFORMATION: n is a, c, g, or u
<220> FEATURE:
```

```
<221> NAME/KEY: modified_base
<222> LOCATION: (7)..(7)
<223> OTHER INFORMATION: n= pseudouridine
<220> FEATURE:
<221> NAME/KEY: misc_feature
<222> LOCATION: (7)..(7)
<223> OTHER INFORMATION: n is a, c, g, or u

<400> SEQUENCE: 17 ncuaaanc                                                                     8

<210> SEQ ID NO 18
<211> LENGTH: 35
<212> TYPE: DNA
<213> ORGANISM: Homo sapiens
<220> FEATURE:
<221> NAME/KEY: modified_base
<222> LOCATION: (15)..(15)
<223> OTHER INFORMATION: n= pseudouridine
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (35)..(35)
<223> OTHER INFORMATION: Base at position 35 is coupled to puromycin

<400> SEQUENCE: 18
uggagguccu gugtncgauc cacagaauuc gcacc                                      35

<210> SEQ ID NO 19
<211> LENGTH: 21
<212> TYPE: RNA
<213> ORGANISM: Homo sapiens
<220> FEATURE:
<221> NAME/KEY: modified_base
<222> LOCATION: (9)..(9)
<223> OTHER INFORMATION: n= pseudouridine
<220> FEATURE:
<221> NAME/KEY: misc_feature
<222> LOCATION: (9)..(11)
<223> OTHER INFORMATION: n is a, c, g, or u
<220> FEATURE:
<221> NAME/KEY: modified_base
<222> LOCATION: (10)..(10)
<223> OTHER INFORMATION: n= pseudouridine
<220> FEATURE:
<221> NAME/KEY: modified_base
<222> LOCATION: (11)..(11)
<223> OTHER INFORMATION: n= pseudouridine

<400> SEQUENCE: 19
ccccccgann nagacccccc c                                                     21

<210> SEQ ID NO 20
<211> LENGTH: 26
<212> TYPE: RNA
<213> ORGANISM: Homo sapiens

<400> SEQUENCE: 20
auauauauau auauauauau gggggg                                                26

<210> SEQ ID NO 21
<211> LENGTH: 26
<212> TYPE: DNA
<213> ORGANISM: Homo sapiens

<400> SEQUENCE: 21
ccccccatat atatatatat atatat                                                26
```

<210> SEQ ID NO 22
<211> LENGTH: 31
<212> TYPE: RNA
<213> ORGANISM: Homo sapiens

<400> SEQUENCE: 22
gcggauuuag cucaguuggg agagcgccag a                                       31

<210> SEQ ID NO 23
<211> LENGTH: 31
<212> TYPE: RNA
<213> ORGANISM: Homo sapiens

<400> SEQUENCE: 23
ggggcuuuag cucaguuggg agagcgccag a                                       31

<210> SEQ ID NO 24
<211> LENGTH: 36
<212> TYPE: RNA
<213> ORGANISM: Homo sapiens
<220> FEATURE:
<221> NAME/KEY: misc_feature
<222> LOCATION: (35)..(36)
<223> OTHER INFORMATION: bases at 35 and 36 are joined by a crosslinker

<400> SEQUENCE: 24
gcggauuuag cucaguuggg agagcgccag acucua                                  36

<210> SEQ ID NO 25
<211> LENGTH: 36
<212> TYPE: RNA
<213> ORGANISM: Homo sapiens
<220> FEATURE:
<221> NAME/KEY: misc_feature
<222> LOCATION: (35)..(36)
<223> OTHER INFORMATION: bases at 35 and 36 are joined by a crosslinker

<400> SEQUENCE: 25
ggggcuuuag cucaguuggg agagcgccag acucua                                  36

<210> SEQ ID NO 26
<211> LENGTH: 61
<212> TYPE: RNA
<213> ORGANISM: Homo sapiens
<220> FEATURE:
<221> NAME/KEY: misc_feature
<222> LOCATION: (59)..(60)
<223> OTHER INFORMATION: bases at 59 and 60 are joined by a crosslinker

<400> SEQUENCE: 26
ggguuaacuu uagaaggagg ucgccaccau gguuaaaaug aaaaugaaaa ugaaaaugua        60
g                                                                        61

<210> SEQ ID NO 27
<211> LENGTH: 55
<212> TYPE: RNA
<213> ORGANISM: Homo sapiens

<400> SEQUENCE: 27
ggguuaacuu uagaaggagg ucgccaccau gguuaaaaug aaaaugaaaa ugaaa             55

<210> SEQ ID NO 28
<211> LENGTH: 61
<212> TYPE: DNA

```
<213> ORGANISM: Homo sapiens
<220> FEATURE:
<221> NAME/KEY: misc_feature
<222> LOCATION: (59)..(60)
<223> OTHER INFORMATION: bases at 59 and 60 are joined by a crosslinker
<220> FEATURE:
<221> NAME/KEY: misc_feature
<222> LOCATION: (61)..(61)
<223> OTHER INFORMATION: base at 60 comprises a biotin label

<400> SEQUENCE: 28
ggguuaacuu uagaaggagg ucgccaccau gguuaaaaug aaaaugaaaa ugaaaaugua      60
g                                                                     61

<210> SEQ ID NO 29
<211> LENGTH: 61
<212> TYPE: DNA
<213> ORGANISM: Homo sapiens

<400> SEQUENCE: 29
ggguuaacuu uagaaggagg ucgccaccau gguuaaaaug aaaaugaaaa ugaaaaugua      60
g                                                                     61

<210> SEQ ID NO 30
<211> LENGTH: 21
<212> TYPE: RNA
<213> ORGANISM: Homo sapiens
<220> FEATURE:
<221> NAME/KEY: misc_feature
<222> LOCATION: (1)..(6)
<223> OTHER INFORMATION: n is a, c, g, or u
<220> FEATURE:
<221> NAME/KEY: modified_base
<222> LOCATION: (9)..(11)
<223> OTHER INFORMATION: n= pseudouridine
<220> FEATURE:
<221> NAME/KEY: misc_feature
<222> LOCATION: (9)..(11)
<223> OTHER INFORMATION: n is a, c, g, or u
<220> FEATURE:
<221> NAME/KEY: misc_feature
<222> LOCATION: (15)..(21)
<223> OTHER INFORMATION: n is a, c, g, or u

<400> SEQUENCE: 30
nnnnnngann nagannnnnn n                                               21

<210> SEQ ID NO 31
<211> LENGTH: 35
<212> TYPE: DNA
<213> ORGANISM: Homo sapiens
<220> FEATURE:
<221> NAME/KEY: modified_base
<222> LOCATION: (15)..(15)
<223> OTHER INFORMATION: n= pseudouridine
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (35)..(35)
<223> OTHER INFORMATION: Base at position 35 is coupled to puromycin

<400> SEQUENCE: 31
uggagguccu gugtncgauc cacagaauuc gcacc                                35

<210> SEQ ID NO 32
<211> LENGTH: 36
```

```
<212> TYPE: DNA
<213> ORGANISM: Homo sapiens
<220> FEATURE:
<221> NAME/KEY: modified_base
<222> LOCATION: (15)..(15)
<223> OTHER INFORMATION: n= pseudouridine
<220> FEATURE:
<221> NAME/KEY: misc_feature
<222> LOCATION: (15)..(15)
<223> OTHER INFORMATION: n is a, c, g, t or u

<400> SEQUENCE: 32
uggagguccu gugtncgauc cacagaaucu ccacca                                    36
```

METHOD FOR MAKING TARGETED THERAPEUTIC AGENTS

RELATED APPLICATIONS

This application is a continuation of U.S. patent application Ser. No. 11/813,849 filed on May 2, 2008, which claims priority to International Application Number PCT/US2006/000956 filed on Jan. 12, 2006, which claims priority to U.S. Provisional Application No. 60/643,191 filed on Jan. 12, 2005.

BACKGROUND OF THE INVENTION

1. Field of the Invention

The present invention relates to methods for making therapeutics tailored to individual patients or sub-populations of patients, as well as methods of using such therapeutics to treat malignancies, pathogenic infections, and other conditions, and to reduce or prevent transplant rejection.

2. Description of the Related Art

Many malignant cells display epitopes that are specific not only to the type of malignancy but also to the individual patient. In some aspects, the present invention is directed to therapeutics that can be targeted to patient-specific epitopes, such as those displayed on malignant lymphocytes.

Lymphocytes are critical to the immune system of vertebrates. Lymphocytes are produced in the thymus, spleen and bone marrow (adult) and represent about 30% of the total white blood cells present in the circulatory system of humans (adult). There are two major sub-populations of lymphocytes: T cells and B cells. T cells are responsible for cell-mediated immunity, while B cells are responsible for antibody production (humoral immunity). In a typical immune response, T cells are activated when the T cell receptor binds to fragments of an antigen that are bound to major histocompatibility complex ("MHC") glycoproteins on the surface of an antigen presenting cell; such activation causes release of biological mediators ("interleukins") which, in essence, stimulate B cells to differentiate and produce antibody ("immunoglobulins") against the antigen.

The etiology of hematological cancers such as lymphomas, leukemias and multiple myelomas varies or is unknown. Suspected causes range from viral and chemical exposure to familial propensities. A common denominator in these cancers however, is that they all begin with a malignantly transformed B-cell or T-cell which divides to form a clone of cells that express the same Fab idiotype on the immunoglobulin proteins they express on their surface. One of the difficulties in treating these cancers is that each cancer expresses a unique idiotype. Developing a therapeutic treatment that effectively and selectively treats all possible idiotypes has therefore been elusive.

Conventional treatments for hematological cancers typically involve procedures that destroy all blood producing cells in the bone marrow, including the malignant clone, followed by bone marrow replacement with stem cells isolated from the patient or bone marrow from a matched donor to reconstruct the blood producing system. These treatments are highly invasive and marginally curative. One approach involves treatment with monoclonal antibody vaccines that recognize cell surface proteins utilized as "markers" for identification. Therapeutics adopting this approach include Compath-H (Alemtuzumab), HLL2 (Epartuzumab), Hu1D10, and Rituximab, (e.g., U.S. Pat. No. 6,455,043). However, a serious limitation with these monoclonal antibody based therapeutics is that the targeted cell surface antigens are often found on both normal as well as malignant cells. In addition, because of the difficulties in producing human monoclonal antibodies, monoclonal antibody vaccines typically utilize "Chimeric" antibodies, i.e., antibodies which comprise portions from two or more different species (e.g., mouse and human). Repeated injections of such foreign antibodies can lead to the induction of immune responses leading to harmful hypersensitivity reactions. For murine-based monoclonal antibodies, this is often referred to as a Human Anti-Mouse Antibody response ("HAMA" response). Patients may also develop a Human Anti-Chimeric Antibody response ("HACA" response). HAMA and HACA can attack "foreign" antibodies so that they are, in effect, neutralized before they reach their target site(s). A further drawback to monoclonal antibody vaccines is the time and expense required to produce monoclonal antibodies. This is particularly problematic considering that targeted epitopes, such as CD20, CD19, CD52w, and anti-class II HLA can readily mutate to form new tumors that are resistant to previous therapeutics (see e.g., Clinical Cancer Research, 5:611-615, 1999). Thus, there is a need in the art for effective, low cost therapeutics for treating malignancies by selectively targeting an individual's cancerous cells over benign cells.

Like malignant cells, the cells of transplanted tissues and organs display cell-surface epitopes that are differentially expressed in transplanted cells relative to native cells. In some aspects, the present invention is directed to therapeutics that can be targeted to the cells of transplanted tissues or organs by recognition of such variable epitopes. Transplant rejection is caused by an immune response to alloantigens on the transplanted cells, which are proteins specific for an individual patient (including the donor), and which are thus perceived as foreign by the recipient. The most common alloantigens involved in transplant rejections are MHC (major histocompatibility complex) molecules, which are expressed on the surface of transplanted cells and are highly polymorphic among individuals. Foreign MHC molecules are recognized by the recipient's immune system, causing an immune response that leads to rejection of the transplant.

One pathway through which the immune system rejects transplanted tissues is complement-mediated immunity, which can be activated by binding of C1 (a first component of complement) to an immune complex consisting of an MHC antigen on a transplanted cell and the recipient's natural antibody against the MHC antigen. Activation of the pathway results in the assembly of enzymes called C3 convertases, which cleave the complement component C3 to form C3a and C3b. Some of the C3b molecules then bind to the C3 convertases to cleave C5 to C5a and C5b. The biological activities of the complement system, in turn, are derived from the cleavage products of C3 and C5. Another subcomponent of the complement system, C1q, is involved in the initial steps of complement activation. To date, methods for treating transplant rejection by modulating complement-mediated immunity have suffered from side effects associated with non-selectivity, due, for example, to the suppression of all complement-mediated immune responses by a therapeutic agent, which eliminates an important component of the immune system's ability to protect against foreign molecules.

Accordingly, there is a need in the art for effective, low cost therapeutics for reducing or preventing transplant rejection by selectively inhibiting the body's immune response against transplanted cells while retaining protection against foreign pathogens, and/or by selectively destroying particular cell types that stimulate a larger immune response.

SUMMARY OF THE INVENTION

In various aspects, methods are provided herein for developing targeted therapeutics useful in treating a wide range of conditions by targeting cell-surface markers (e.g., epitopes, idiotypes, and the like) or other molecules that are differentially expressed by, or in close proximity to, malignant cells, pathogens, transplanted cells, and/or other entities targeted for treatment. Also provided are methods for treating a disease or condition by administering a therapeutic produced by methods described herein.

In some preferred embodiments, methods provided herein utilize novel techniques for linking proteins to their corresponding mRNAs, and screening the protein-mRNA complexes for binding to a molecular target associated with one or more etiological determinants. In various preferred embodiments, therapeutics provided herein are designed to recognize molecular targets that are differentially expressed in an individual patient seeking treatment, or in a sub-population of patients, such as patients diagnosed with a specific strain or subtype of a disease or condition. Proteins having high affinity for a target of interest are preferably isolated and linked to one or more therapeutic agents effective against the disease being treated (e.g., cytotoxic agents), to produce a variety of targeted therapeutics. Advantageously, the rapid and efficient identification, isolation, and production of proteins capable of recognizing targets of interest provides effective, low cost methods for the production of patient- and/or disease-specific therapeutics. In various embodiments, methods provided herein beneficially allow a wide range of diseases and conditions to be treated with tailored therapeutics, within the context of existing health care budgets and resource allocations.

In various aspects, methods are provided herein for producing tailored therapeutics for treating cancers and other conditions, wherein the tailored therapeutics comprise a "targeting domain" that binds to a molecular target associated with a disease or condition selected for treatment, and a "therapeutic agent" capable of treating or preventing said disease or condition. In some preferred embodiments, the targeting domain is tailored to recognize targets that are differentially expressed in particular patients or sub-populations of patients, while in these and/or other embodiments, the therapeutic agent does not require substantial tailoring to individual patients or sub-populations of patients. This "modular" architecture advantageously allows for the creation of individualized therapeutics by tailoring only the small portion of the administrable therapeutic comprising the targeting domain, which can then be used to enhance the efficacy of a variety of pre-existing or easily prepared therapeutic agents.

In some preferred embodiments, the targeting domain is tailored to bind an epitope selectively or preferentially expressed by cancerous cells relative to non-cancerous cells in a patient seeking treatment, and the therapeutic agent is an antibody or other molecule (hereinafter referred to as the "immune effector") capable of stimulating an immune response in the patient. In some preferred embodiments, the targeted epitopes are substantially absent from non-cancerous cells, and the therapeutic agent does not otherwise substantially bind to non-cancerous cells. In some preferred embodiments, the cancer is a hematological cancer, such as a lymphoma (e.g., non-Hodgkin's lymphoma), a leukemia, or a multiple myeloma, wherein cancerous and/or malignant cells express a patient-specific epitope that can be an idiotype.

In various embodiments, the therapeutic agent is linked, fused, or derivatized, directly or indirectly, to the targeting domain to form the modular therapeutic. In some embodiments, an immune effector is covalently linked to a target-binding domain, while in other embodiments it is non-covalently bound. In some embodiments, the target-binding domain is part of a bifunctional protein comprising a target-binding domain fused to a second domain that binds the immune effector. The immune effector-binding domain may comprise an epitope recognized by variable regions of an antibody, or a molecule that binds other regions of an antibody, such as the Fc region. The immune effector-binding domain may also comprise a peptide sequence designed to tightly bind the immune effector (see e.g., FIG. 9). The bifunctional protein may comprise a fusion protein, or the two domains can be covalently or non-covalently linked. The target-binding domain and the immune effector binding domain can be directly linked, or indirectly linked, for example via a flexible linker peptide.

In other aspects, the invention provides methods for preparing a therapeutic for treating a cancer comprising isolating complexes of expressed mRNA molecules and their nascent polypeptides from an mRNA expression library; screening the protein-mRNA complexes for binding to a molecular target associated with an etiological determinant, such as an epitope displayed by a cancerous cell; isolating and expressing mRNA encoding a protein that binds the target epitope; and derivatizing the target epitope-binding protein (or derivatives, fragments or subunits thereof) to a therapeutic agent, such as an antibody capable of eliciting an immune response against the target. In some embodiments, the preparation of the therapeutic further comprises allowing isolated mRNA encoding a target-binding domain to undergo in vitro evolution, selective mutagenesis, and/or other methods known in the art to identify and isolate mRNAs exhibiting stronger or more effective binding to the target epitope, as described in more detail below.

In yet further aspects, the invention provides methods for treating a disease or condition, such as a cancer, comprising identifying a target epitope or other molecule specifically or preferentially expressed on, or in close proximity to, an etiological determinant of the condition targeted for treatment, in a patient in need of treatment; isolating a protein that binds the target, but does not bind substantially to non-targets; linking the target-binding protein (or derivatives, fragments or subunits thereof) to a therapeutic agent, such as an antibody capable of eliciting an immune response in the subject of interest; and administering the therapeutic to the patient in an amount and for a time sufficient to treat the condition targeted for treatment.

In a still further aspect, the invention provides methods for identifying proteins that bind cancer cell target epitopes, or other etiological determinants, comprising isolating complexes of expressed mRNA molecules and their nascent polypeptides from an mRNA expression library; screening the protein-mRNA complexes for binding to a target epitope displayed by a cancerous cell; isolating and expressing mRNA encoding a protein that binds the target epitope; and derivatizing the target epitope-binding protein (or derivatives, fragments or subunits thereof) to an antibody capable of eliciting an immune response. In some embodiments, the methods may further comprise allowing isolated mRNA encoding a target epitope-binding protein to undergo in vitro evolution, selective mutagenesis, or other methods known in the art to identify and isolate mRNAs exhibiting stronger or more effective binding to the target epitope.

In yet another aspect, the invention provides a kit for developing an individualized therapeutic for the treatment of a disease or condition characterized by the expression of disease- and/or patient-specific etiological determinants. In some preferred embodiments, a kit is provided for developing patient-specific therapeutics for the treatment of a cancer, including solid tumors and hematological cancers, wherein the therapeutics are targeted to a unique cell-surface epitope differentially expressed on the surface of cancerous and/or malignant cells.

In an additional aspect, the invention provides therapeutics and methods for reducing or preventing transplant rejection. In some embodiments, the target-binding protein binds to cell surface antigens displayed by transplanted cells, such as MHC antigens, and the therapeutic agent (e.g., the immune effector) comprises a protein or other molecule that binds to and inhibits one or more molecular determinants of the immune response. In some preferred embodiments, the immune effector binds the C1q or C3 components of the complement system to thereby inhibit the activation of complement-mediated immunity. In other embodiments, the immune effector stimulates an immune response to eliminate transplanted cells bearing "foreign" MHC or other antigens. In further embodiments, the therapeutic agent ablates or prevents the clonal expansion of lymphocyte subpopulations expressing specific epitopes, for example epitopes that recognize MHC antigens.

The invention further provides methods and kits for inhibiting transplant rejection that are essentially similar to those described above for treating malignancies.

Further aspects of the invention provide therapeutics, methods and kits, essentially similar to those described above, wherein the target-binding domain is selected to bind one or more variable epitopes expressed by a disease-causing pathogen, or one or more cells infected by a disease-causing pathogen, and the therapeutic agent comprises an anti-pathogenic drug, such as an antibiotic or other cytotoxic agent. In some embodiments, the pathogen is a virus, such as HIV.

In various aspects, methods provided herein allow for the rapid and cost-effective creation of individualized therapeutics. The following detailed description illustrates various aspects of the invention as they relate to particular applications. However, the description applies equally to the development and use of therapeutics and methods for the treatment of a wide variety of conditions, including but not limited to, the treatment of malignancies, the reduction and elimination of pathogens, the reduction and/or prevention of transplant rejection, and in general, the treatment of any condition involving a therapeutic target which exhibits differential binding characteristics relative to non-targeted cells or molecules.

These and other objects and features of the invention will become more fully apparent when the following detailed description is read in conjunction with the accompanying drawings.

DETAILED DESCRIPTION OF THE PREFERRED EMBODIMENT

Figure 1:
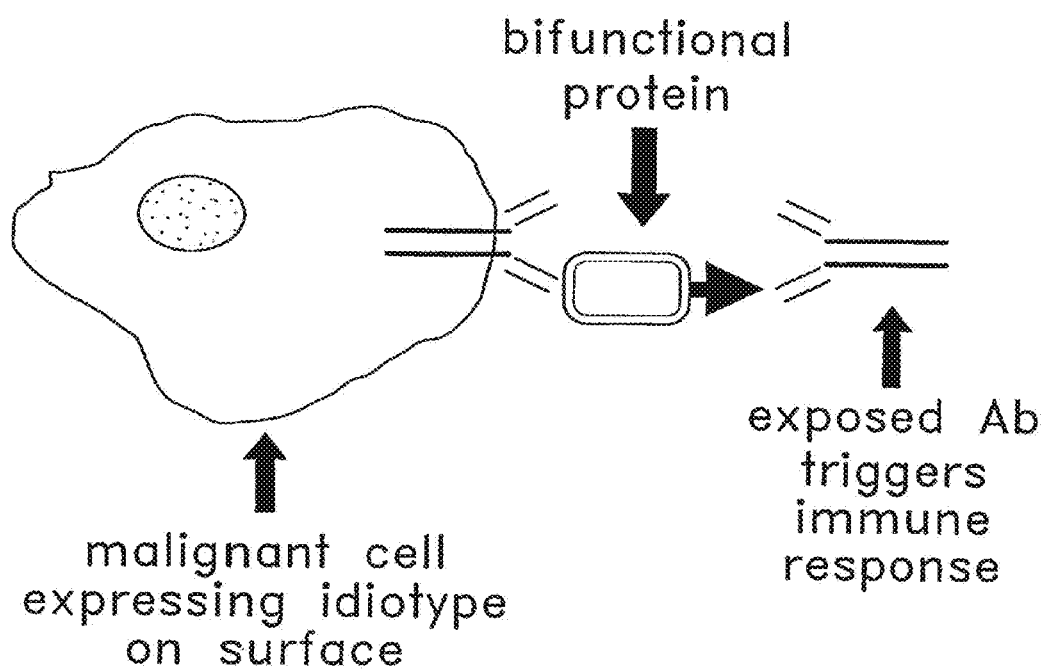
FIG. 1. Complex comprising a target epitope-binding protein and an immune effector antibody reacted with a malignant cell via the Fab idiotype expressed on the cell surface.

The terms "T lymphocyte" and "T cell" as used herein encompass any cell within the T lymphocyte lineage from T cell precursors to mature T cells.

The terms "B lymphocyte" and "B cell" encompasses any cell within the B cell lineage from B cell precursors, such as pre-B cells, to mature B cells and plasma cells.

Immunoglobulin molecules consist of heavy (H) and light (L) chains, which comprise highly specific variable regions at their amino termini. The variable (V) regions of the H ($V_H$) and L ($V_L$) chains combine to form the unique antigen recognition or antigen combining site of the immunoglobulin (Ig) protein. The variable regions of an Ig molecule contain determinants (i.e., molecular shapes) that can be recognized as antigens or idiotypes.

The term "epitope" refers to the set of antigenic or epitopic determinants (i.e., idiotopes) of an immunoglobulin V domain (i.e., the antigen combining site formed by the association of the complementarity determining regions or $V_H$ and $V_L$ regions).

The term "idiotope" refers to a single idiotypic epitope located along a portion of the V region of an immunoglobulin molecule.

The term "immune effector" refers to a molecule, or derivatives, fragments, or subunits thereof, able to stimulate an immune response in the subject being treated, and may comprise an antibody, or derivatives, fragments, or subunits thereof, or a non-antibody molecule.

An "adjuvant" is a compound which enhances or stimulates the immune response when administered with one or more antigen(s).

"Malignant cells" refers to cells, which if left untreated, give rise to a cancer.

The terms "protein," "peptide," and "polypeptide" are defined herein to mean a polymeric molecule of two or more units comprised of amino acids in any form (e.g., D- or L-amino acids, synthetic or modified amino acids capable of polymerizing via peptide bonds, etc.), and these terms may be used interchangeably herein.

Provided herein, are methods for producing individualized therapeutics that are tailored to specific patients, or to sub-populations of patients suffering from a particular disease or condition. In various embodiments, the therapeutics are comprised of a "modular" architecture that allows tailoring of a small protein domain (the "target-binding domain") to bind one or more patient- and/or disease-specific markers, and use of the tailored domain to direct a variety of existing or easily produced therapeutics that are effective against the condition targeted for treatment. The targeted disease markers can comprise any type of molecule, or portion or derivative thereof, or complex of molecules, including but not limited to, proteins, nucleic acids, lipids, chemical compounds, polymers, and metals, as well as biological structures, such as cell membranes, cytoskeletal elements, receptors, and even entire cells. Advantageously, the markers are expressed on, or in close proximity to, an etiological determinant of the condition targeted for treatment, and activity of the therapeutic agent is focused to disease-causing cells, pathogens, proteins, and/or other determinants of the condition being treated.

In some embodiments, the modular therapeutic is tailored for the treatment of a hematological cancer, and designed to bind to the unique Fab idiotype on the surface of malignant B-cells and/or T-cells. For example, in some preferred embodiments, a therapeutic is provided for the treatment of non-Hodgkin's Lymphoma (NHL), which is a "clonal" B-cell disease, in which all cancerous cells are derived from a single, malignant B-cell. As a result, every NHL cell expresses a common idiotype (comprising the variable domains of surface expressed IgM molecules) that is unique to each patient, which can be targeted by the target-binding portions of the modular therapeutics provided herein. B-cells can be isolated from the lymph nodes, or from peripheral blood, using methods known in the art. For example, in some embodiments, erythrocytes and/or granulocytes may be separated from the B-cells by centrifugation in a liquid having a density intermediate between the groups of cells to be separated. Means of obtaining T-lymphocytes are also well known in the art, such as isolation from the peripheral blood of a patient, and separation on the basis of size and/or density. Extraction of proteins from B-cells and/or T-cells may be performed by any of the many means known in the art. For example, cells may be lysed by a detergent or by mechanical means. If desired, nucleic acids can be removed from the cell preparation by enzymatic digestion or by precipitation with agents such as streptomycin. Such means are well known in the art.

The mechanism of action of a modular therapeutic for treating a hematological cancer prepared according to methods described herein is illustrated in FIG. 1. The administered therapeutic binds to the unique Fab idiotype on the surface of malignant B-cells and/or T-cells, and the etiological determinant of the hematological cancer, with which the idiotype is associated, comprises malignant and/or cancerous cells expressing the targeted idiotype. Binding of the targeting domain to the idiotype effects an immune response that destroys the malignant cells. By itself, the target-binding protein is too small to elicit an immune response, and thus the bound immune effector will not produce an IR in the absence of binding to the targeted idiotype. When the target-binding protein binds to the Fab idiotype on the surface of a malignant cell, the malignant cell acts as a carrier that confers immunogenicity to the target epitope-binding protein, allowing the immune effector to produce an IR that targets the malignant cell. In further embodiments, therapeutics and methods of the invention can also be used to target epitopes that distinguish non hematological cancers.

In various preferred embodiments, targeted markers are differentially expressed (i) in an individual patient, or a defined sub-group of patients, relative to other patients having similar diagnoses, and/or (ii) in association with cells or other molecular targets associated with the etiology of the condition, relative to cells/molecules that are unassociated with the condition and preferably not subjected to the therapeutic agent. Advantageously, the selectivity of tailored therapeutics enhances the efficacy of treatment relative to existing, non-tailored therapeutics, due, for example, to the non-selective activity of non-tailored therapeutics against healthy cells, and/or failure of existing targeted therapeutics to account for inter-patient variability in the targeted marker(s). For example, in the case of hematological cancers, the targeted idiotype is unique to both the patient and to the malignant cells, allowing the activity of the therapeutic agent (effecting an immune response) to be selectively directed to targeted cells, sparing non-cancerous cells. Moreover, because the idiotype is unique to each patient, non-tailored therapeutics would result in a non-selective, or less-selective, therapeutic response.

Examples of cell-surface markers differentially expressed by malignant cells include, but are not limited to: for fluid tumors, stable cell surface antigen epitopes, such as CD-20 and CD-22, and for solid tumors, surface epitopes, such as CD-19 and CD-33, which become internalized upon binding with a mAb. Other differentially expressed cell-surface markers are known in the art, including but not limited to, CD-52w and class II HLA antigens. In some preferred embodiments, the targeted epitope is a cancer cell-specific epitope that is mutated (see e.g., Clinical Cancer Research, 5:611-615, 1999) in the patient targeted for treatment. Advantageously, methods provided herein allow for more efficacious treatment of cancers by allowing the development of individualized therapeutics that target mutated epitopes, which are unique to each patient.

Figure 2:
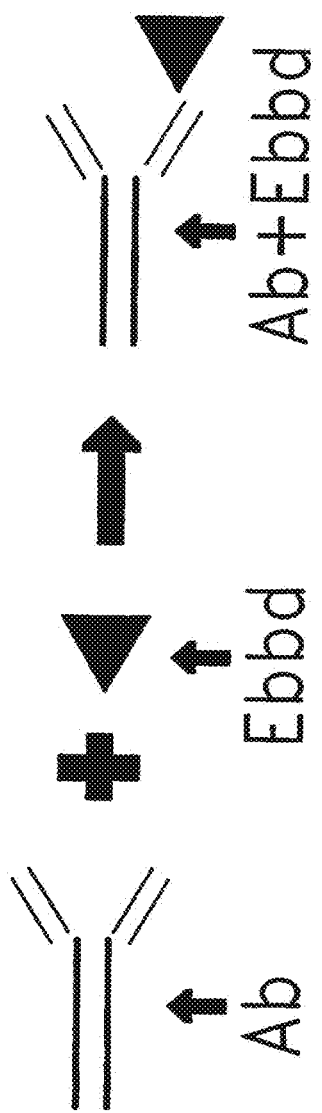
FIG. 2. Illustration of a known human antibody (Ab) to a small human protein (Ebbd). The protein can serve as an epitope that links the antibody (Ab) to the therapeutic. The role of the Ab is to act as an immune effector that ultimately triggers an immune response.

In some preferred embodiments (as shown, e.g., in FIG. 2), the target-binding domain of the modular therapeutic comprises a first sub-domain that binds the target (e.g., a target epitope-binding domain (Tebd)), and a second sub-domain that binds the therapeutic agent (e.g., an immune effector-binding domain (Ebbd)). In some embodiments, the therapeutic agent is an agent that is capable of stimulating an immune response in the subject targeted for treatment, such as an antibody, or a derivative, fragment, or subunit thereof, and the domain that binds the therapeutic agent is a small protein recognized by the therapeutic agent, for example an epitope recognized by a therapeutic agent antibody. Well-characterized antibody-antigen pairs can also be utilized that are known in the art, and are commerically available. Antibodies useful in the invention may be derived from any mammal, or may be a chimeric antibody derived from a combination of different mammals. The mammal may be, for example, a rabbit, a mouse, a rat, a goat, or a human. The antibody is preferably a human antibody. Reactivity of antibodies against a target antigen may be established by a number of well known means, including Western blot, immuno-precipitation, ELISA, and FACS analyses using, as appropriate, Fab idiotype fragments, peptides, idiotype-expressing cells or extracts thereof. The antibody can belong to any antibody class and/or sub-class. The antibodies may also contain fragments from antibodies of different classes and sub-classes, thereby forming a composite.

In various embodiments, human monoclonal antibodies having a desired binding activity are produced using methods known in the art (for review, see Vaughan et al., 1998, Nature Biotechnology 16: 535-539), for example by screening a phage display library, as described, e.g., in Parmley and Smith Gene 73:305-318 (1988), Barbas et al., Proc. Natl. Acad. Sci. USA 88: 7978-7982 (1991), Griffiths et al., EMBO J 13: 3245-3260 (1994), Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993), and Burton and Barbas, Human Antibodies from combinatorial libraries. Id., pp 65-82, all of which are herein incorporated by reference. Typically, clones corresponding to antibodies which produce binding affinities of a desired magnitude are identified, and the DNA is used to produce the antibodies of interest using standard recombinant expression methods.

Fully human monoclonal antibodies may also be produced using transgenic mice engineered to contain human immunoglobulin gene loci, as described in PCT Patent Application WO98/24893 and Jakobovits, 1998, Exp. Opin. Invest. Drugs 7(4): 607-614, herein incorporated by reference. This method avoids the in vitro manipulation required with phage display technology and efficiently produces high affinity authentic human antibodies.

In some embodiments, an antibody against an antigen of interest, such as an immune effector-binding domain, is produced in the patient selected for treatment with the modular therapeutic. For example, in some embodiments, the patient is "vaccinated" with the antigen of interest, and antibodies from the patient against the antigen are selected by binding to the antigen of interest, as described in Zebedee, et al. Proc. Natl. Acad. Sci. USA 89: 3175-3179 (1992), Burton et al., Proc. Natl. Acad. Sci. USA 88: 10134-10137 (1991), and Barbas et al., Proc. Natl. Acad. Sci. USA 89: 10164-20168 (1991).

In some embodiments, additional rounds of screening are performed to increase the affinity of the originally isolated antibody. For example, in some embodiments, the affinity of the antibody is enhanced by affinity maturation, in which hypervariable antibody regions are mutated to produce a large number of combinations, and the corresponding antibody variants are screened via phage display to select antibodies having the desired affinity for the antigen. In further embodiments, the small protein epitope can undergo in vitro evolution, as described in more detail below, to increase its binding affinity for the antibody. Advantageously, in some embodiments, for example those in which antibodies are produced by "vaccinating" a patient, an analogous process is carried out by the host immune system (e.g., via clonal selection) to produce high affinity antibodies specific for the antigen of interest.

In other embodiments, the immune effector comprises a non-antibody molecule capable of stimulating an immune response in the subject receiving treatment. For example, the immune effector may comprise a C3 convertase, as described, e.g., in U.S. Pat. No. 6,268,485 to Farries and Harrison, which is herein incorporated by reference. C3 convertase is an enzyme that catalyzes the proteolytic conversion of C3 protein into C3a and C3b, which conversion comprises a critical step in the generation of the complement system response. C3b binds to cell surfaces near its site of generation, where it mediates phagocytosis and other destructive immune responses. In some embodiments, C3 convertase is modified or derivatized to confer reduced susceptibility to inhibitors, resistance to proteolytic cleavage, enhanced affinity for cofactors, or other modifications that enhance the effectiveness of the enzyme in stimulating a complement-mediated immune response. In some embodiments, the immune effector comprises a C5 convertase, a mannose binding protein (MBP), or another molecule that stimulates complement-mediated immunity.

Figure 9:
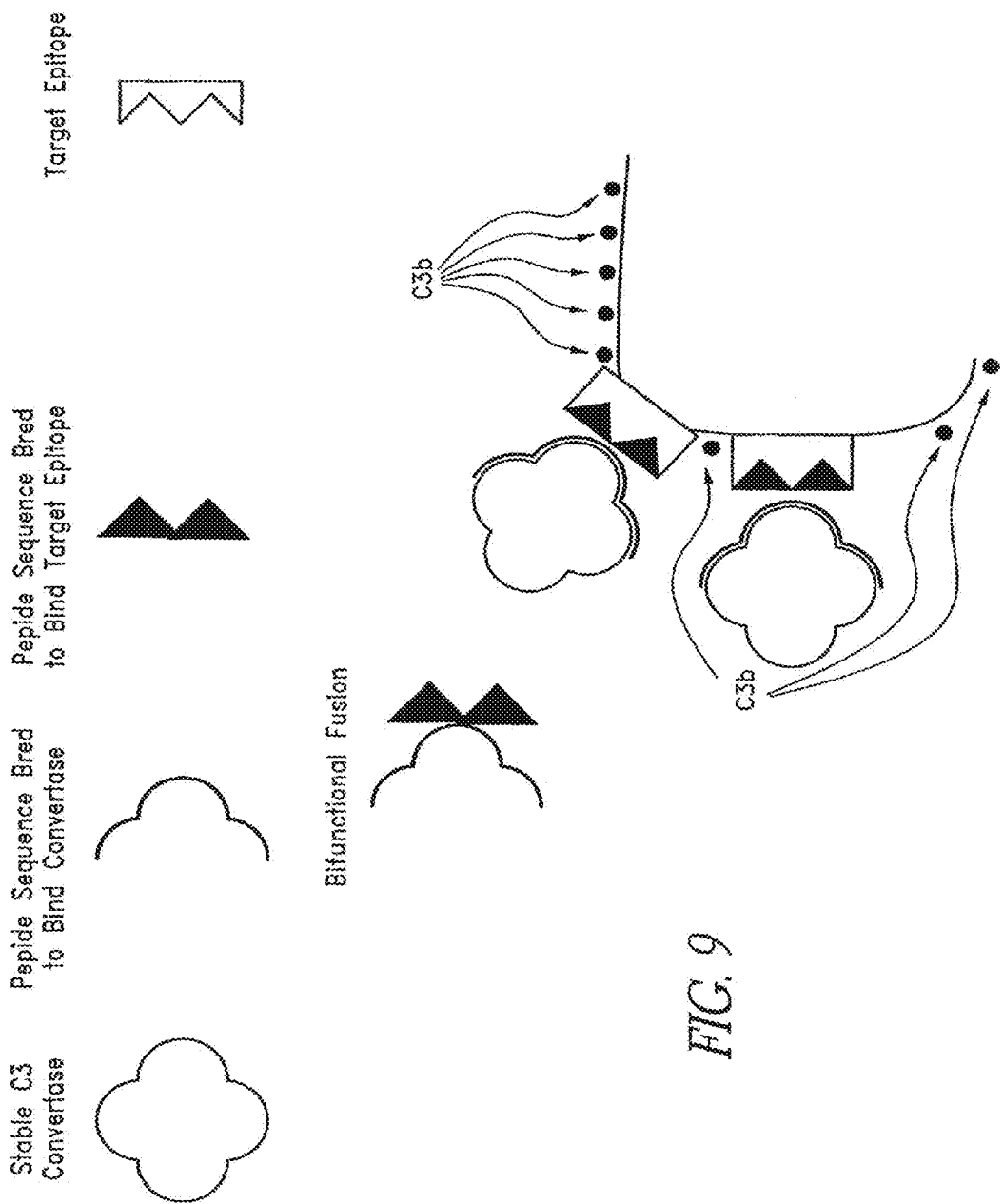

Linking C3 convertase to the therapeutics of the instant invention allows a complement-mediated immune response to be directed to cells, pathogens, pathogen-infected cells, and/or other cells targeted for treatment by binding of the target epitope binding protein to variable epitopes on the surface of the targeted cells. A therapeutic with C3 convertase as the immune effector is illustrated in FIG. 9. In a preferred embodiment, peptide sequences encoding proteins that bind C3 convertase (the immune effector binding protein) and a target epitope (the target epitope binding protein) are identified, isolated, and optionally bred by in vitro evolution or other techniques to increase their affinity to their target ligands. A bifunctional fusion protein is then constructed comprising the target epitope binding domain, and the convertase binding peptide as the immune effector binding domain (Ebbd). The therapeutic is administered to a patient in need of treatment, upon which the target epitope-binding domain binds to the surface of a malignant cell or other target, and the C3 convertase produces a complement-mediated immune response, which includes the production of membrane attack complexes that mediate the destruction of the targeted cell.

Figure 10:
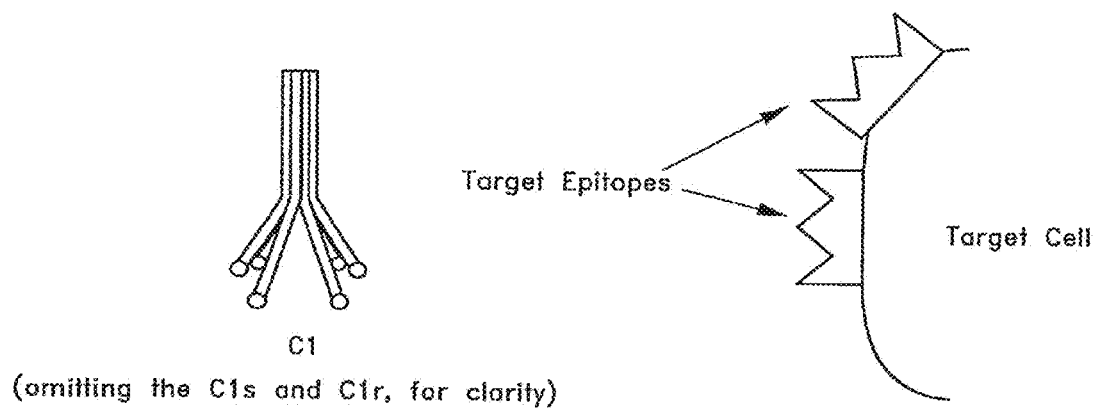
Figure 10:
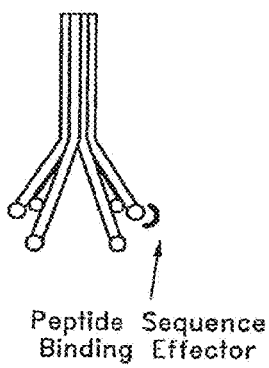
Figure 10:
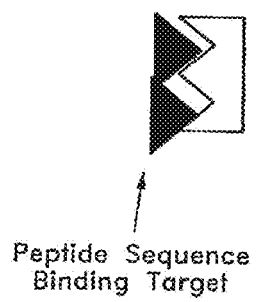
Figure 10:
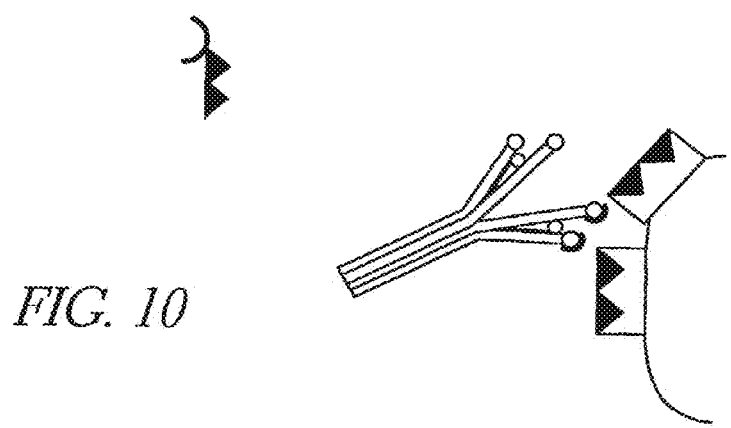
Figure 11:
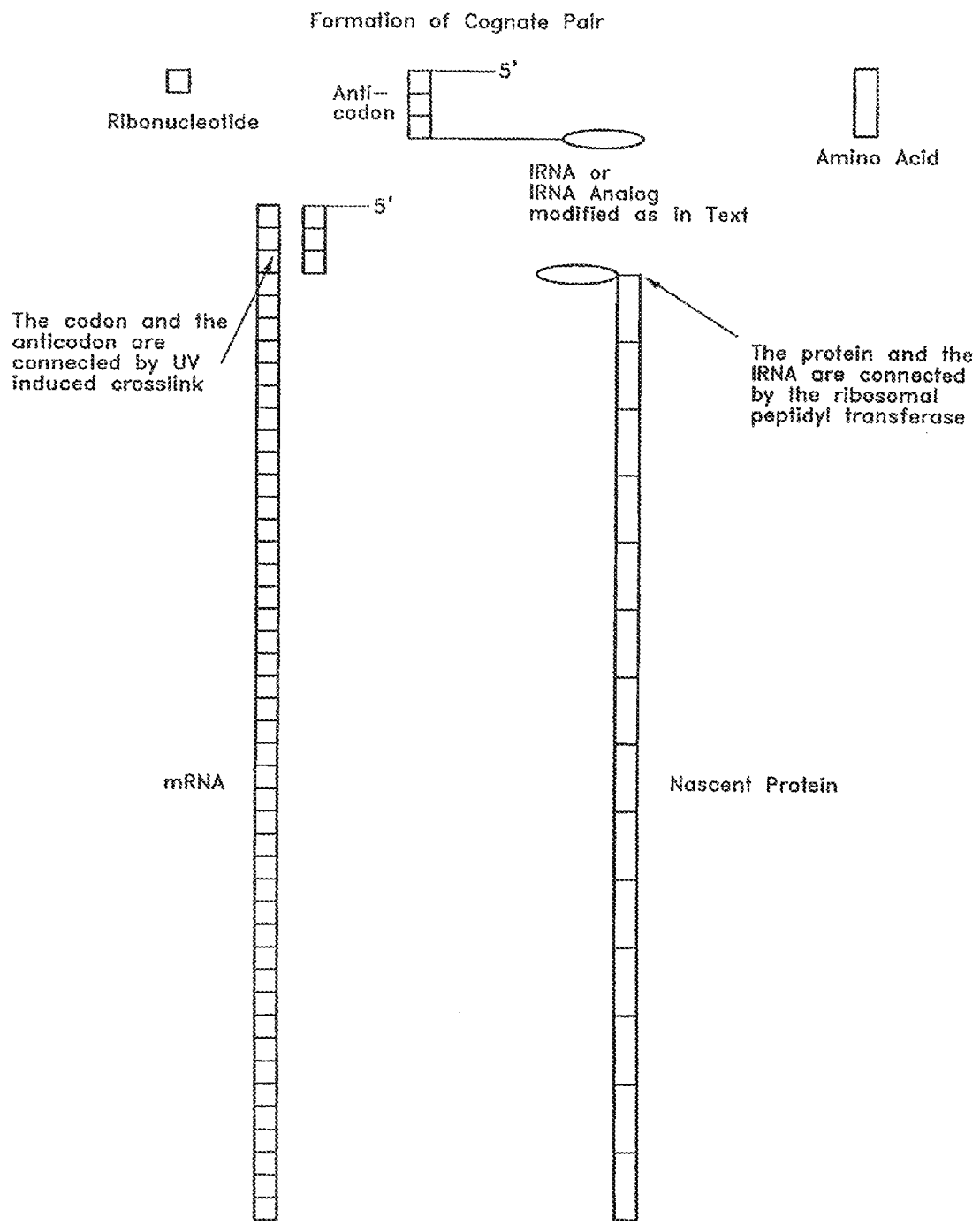
Figure 12:
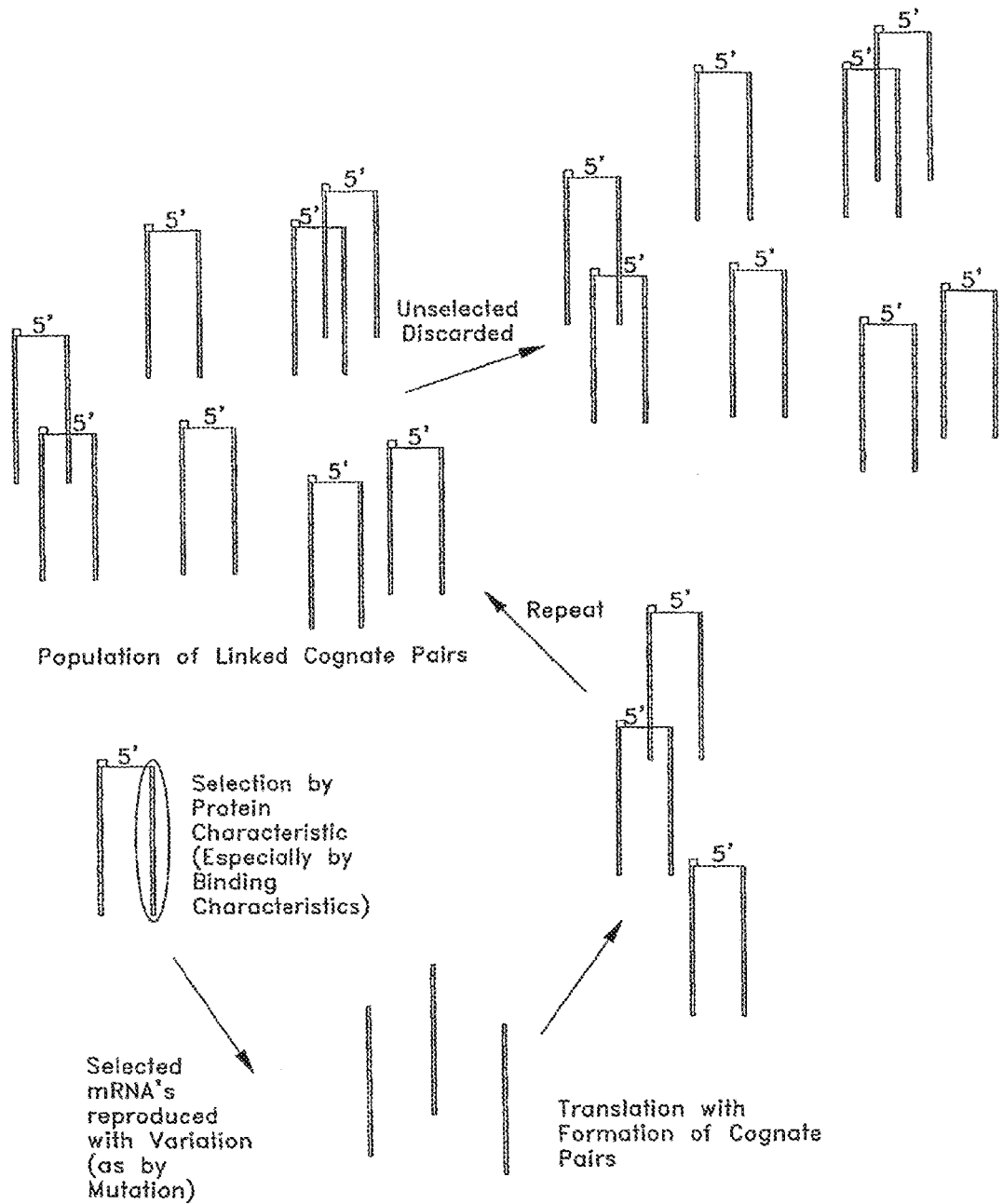
Figure 13:
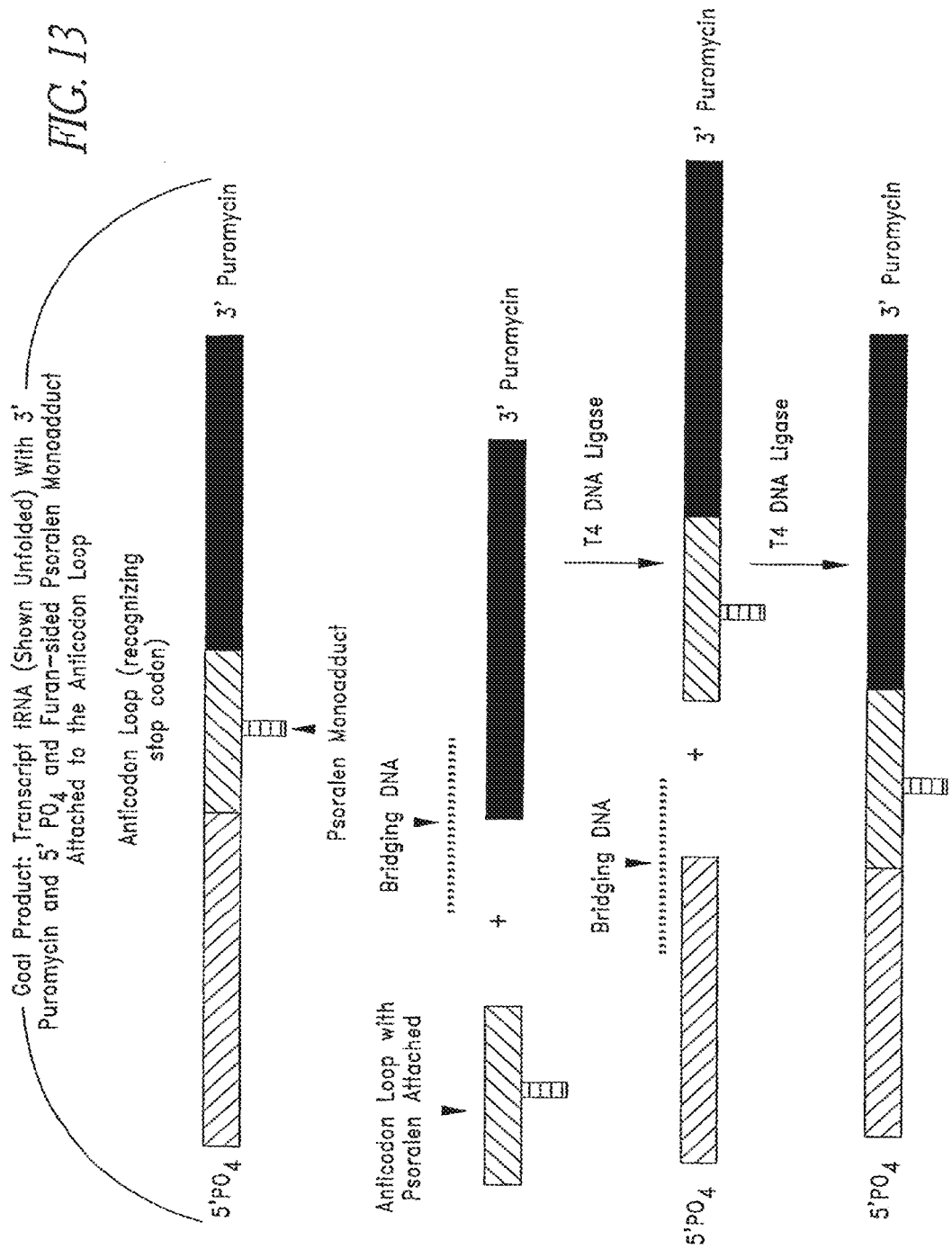
Figure 14:
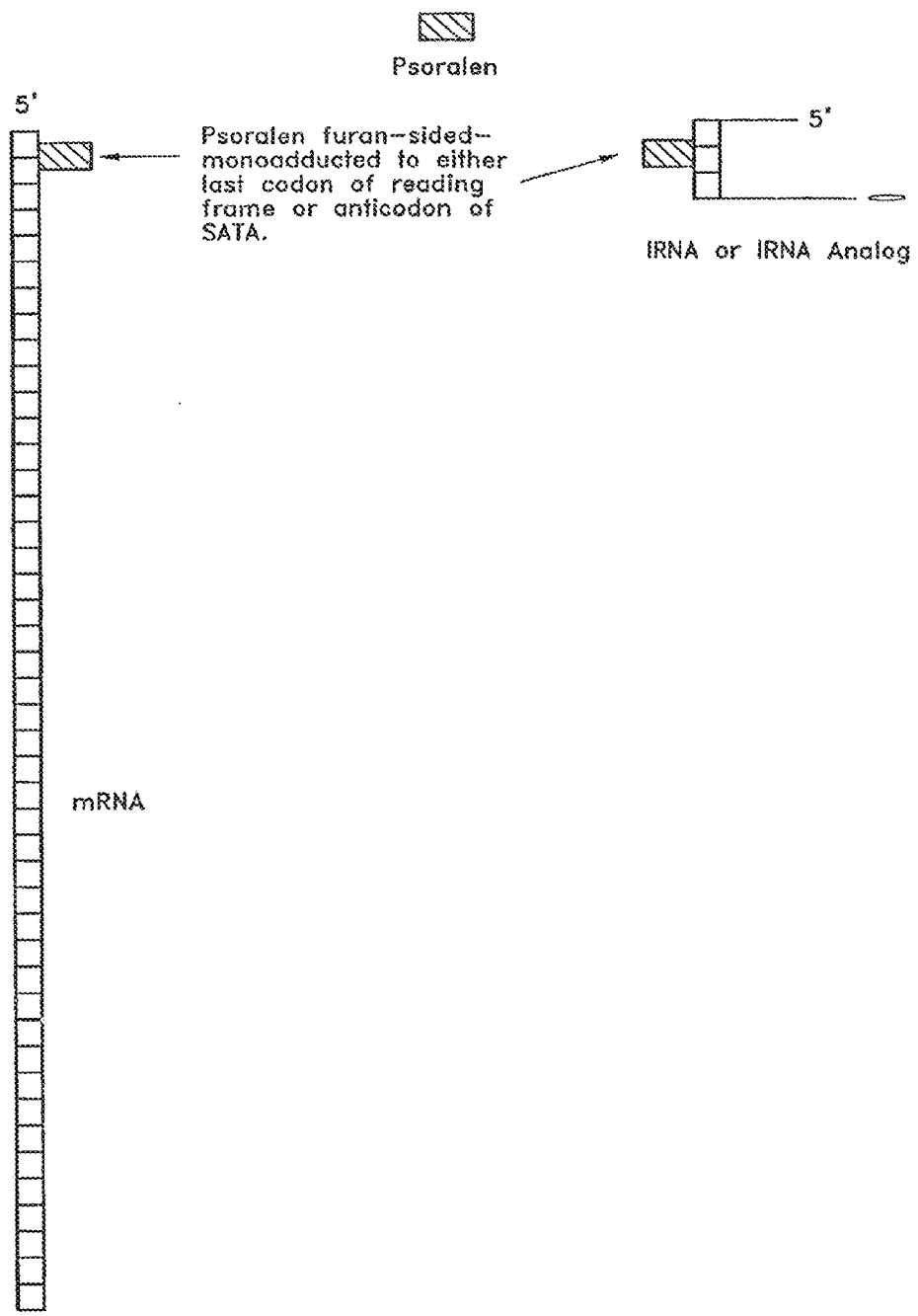
FIG. 14 describes two alternative embodiments by which the crosslinking molecule psoralen can be positioned such that it is capable of linking the mRNA with the tRNA in the methods of the invention. A first embodiment includes linking the crosslinker (e.g., psoralen monoadduct) to the mRNA, and a second embodiment includes linking the crosslinker to the anticodon of the tRNA molecule. The crosslinker can either be monoadducted to the anticodon or the 3' terminal codon of the reading frame for known or partially known messages. This can be done in a separate procedure from translation, e.g., before translation occurs.
Figure 15:
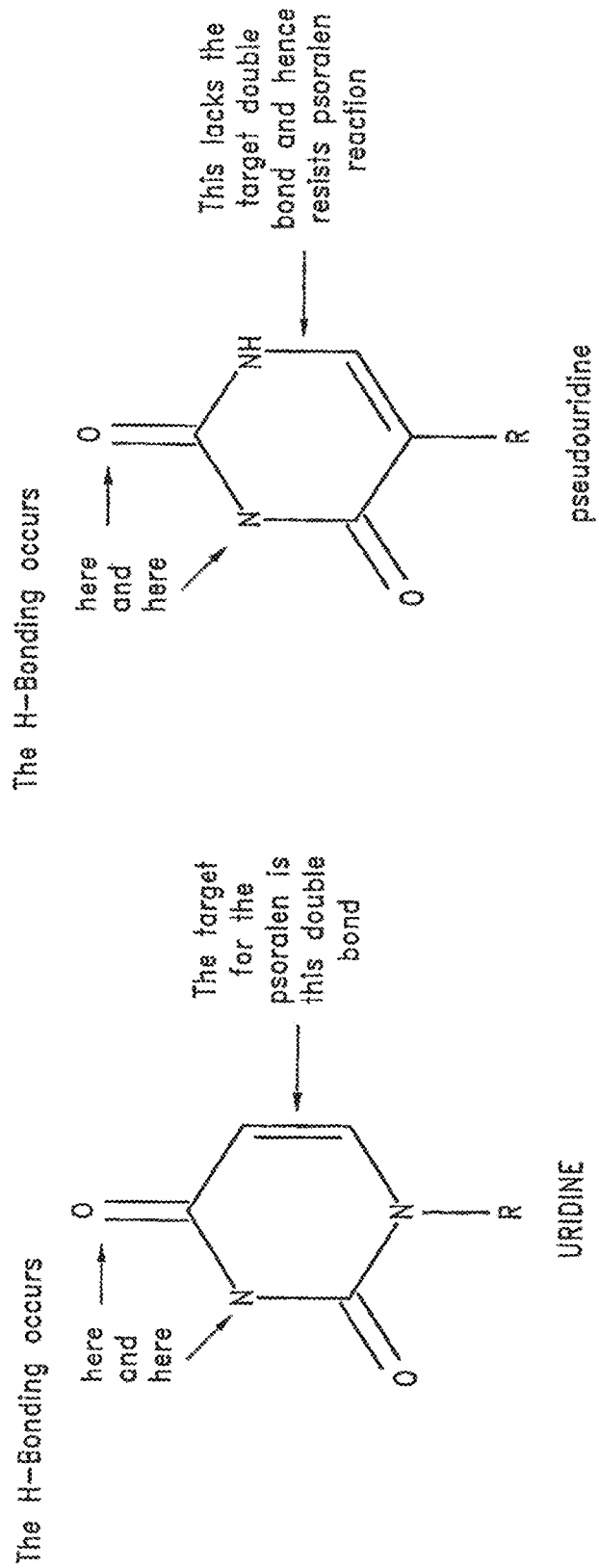
FIG. 15 illustrates the chemical structures for uridine and pseudouridine. Pseudouridine is a naturally occurring base found in tRNA that forms hydrogen bonds just as uridine does, but lacks the 5-6 double bond that is the target for psoralen.
Figure 16:
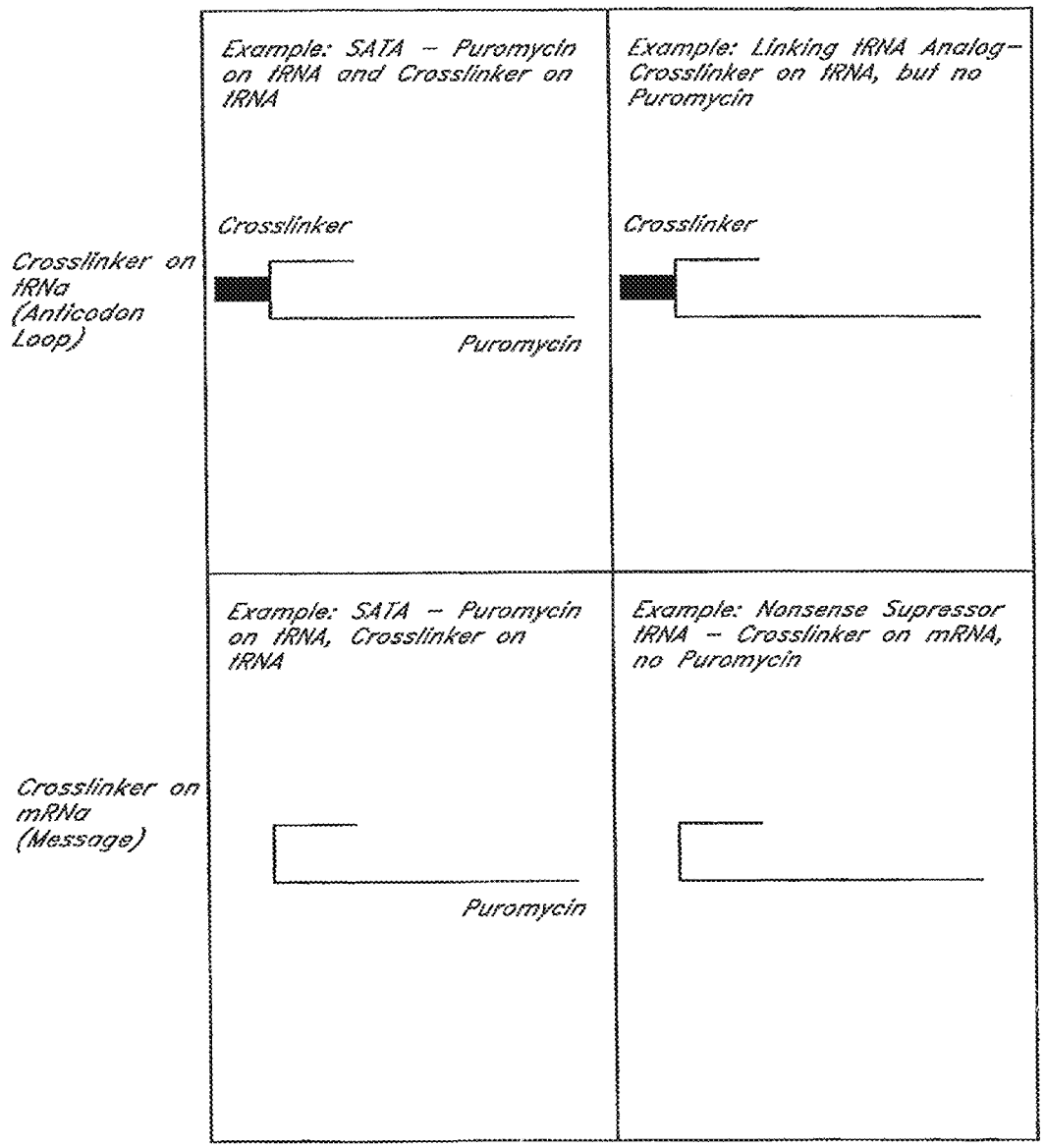
FIG. 16 illustrates some embodiments of the present invention. The SATA, Linking tRNA Analog and Nonsense Suppressor analog, in certain embodiments, are shown.

In some embodiments, the therapeutic comprises a target epitope-binding domain and a C3 convertase binding domain. Upon being administered, such therapeutics bind a target epitope and recruit endogenous C3 convertase to initiate a complement-mediated immune response. Such an approach is illustrated in FIG. 10, which shows a therapeutic in which the immune effector binds the C1 component of the complement system. Upon being administered to a patient in need of treatment, the therapeutic binds to the target epitope and recruits endogenous C1 to the cell surface, where it induces a complement-mediated immune response.

In other embodiments, the immune effector component of the therapeutic binds to and inhibits C1q, C3, C5, and/or other molecules involved in generating complement-mediated immune responses, such as the proteins described in U.S. Pat. No. 5,650,389. Upon being administered to a patient in need of treatment, such therapeutics bind to the target epitope and inhibit the immune response that would otherwise be directed at or near the binding site. For example, in some preferred embodiments, a patient is the recipient of transplanted cells (e.g., stem cells, or cells comprising a transplanted organ), and the targeted therapeutic is capable of recognizing transplanted cells, and inhibiting an immune response against such cells. In further embodiments, targeted therapeutics for the inhibition of transplant rejection comprise a target-binding domain that targets one or more epitopes of immune cells that recognize transplanted cells, for example epitopes that bind MHC antigens on the surfaces of transplanted cells, and the therapeutic agent is an immune effector capable of stimulating an immune response in the patient against the anti-transplant immune cells.

Advantageously, methods provided herein are rapid and cost-effective enough to allow routine creation of individualized therapeutics. Therapeutics according of the invention can preferably be created, from reception of the biopsy material to the completion of the therapeutic, in a matter of weeks and at a cost of several thousand dollars.

A bifunctional fusion protein for use in the invention can be produced according to standard recombinant DNA techniques known to those skilled in the art (e.g., Sambrook, J. et al., Molecular Cloning: A Laboratory Manual, 2nd ed., Cold Spring Harbor Laboratory Press, New York (1989)). In some embodiments, the purified bifunctional protein can be reacted with the immune effector, yielding a conjugated effector-bifunctional protein complex, as shown FIG. 7, which comprises the therapeutic. The bifunctional protein can also be chemically bound to the immune effector through means known in the art.

In some embodiments, a protein coupling agent, such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis-(p-azidobenzoyl)hexanediamine), bis-diazonium derivatives (such as bis-(p-diazoniumbenzoyl)-ethyl-enediamine), diisocyanates (such as tolyene 2,6-diisocyanate), or bis-active fluorine compounds (such as 1,5-difluoro-2,4-dinitrobenzene), is used to link two or more protein components comprising the therapeutic.

In some embodiments, a recombinant fusion protein is prepared by: linking a first polynucleotide sequence encoding a target-epitope-binding protein, or derivatives, fragments or subunits thereof, to a second polynucleotide sequence encoding an epitope or other protein that binds the immune effector to generate a chimeric coding sequence; subcloning the chimeric coding sequence into an expression vector; transfecting a cell with the expression vector; and purifying the fusion protein expressed by the transfected cell. In some embodiments, the chimeric polynucleotide can include an initiation sequence appropriate for prokaryotic and/or eukaryotic in vitro translation systems, and/or a selectable marker.

In some embodiments, the bifunctional protein complex is made by in vitro translation of an mRNA oligo that includes the mRNA encoding both proteins and, in some embodiments, the major histocompatibility complex I and/or II. The cDNA for the mRNA sequences can be synthesized or obtained commerically, and transcribed by PCR to obtain sufficient mRNA, as shown in FIG. 3. In various embodiments, the oligo is formed by ligating mRNA encoding the immune effector-binding domain and the mRNA encoding the target epitope-binding domain. In some cases this fusion can be connected through an mRNA bridge that codes for hydrophilic amino acids, as illustrated in FIG. 6. The mRNA can then be translated in vitro using prokaryotic or eukaryotic translation systems, and the resultant bifunctional protein can purified by gel electrophoresis or any other method known in the art.

The present fusion proteins can also comprise one or more numerous other components that enhance the utility of the chimeric proteins. For example, the proteins can be designed to contain an epitope tag useful, for example, to facilitate purification of the fusion proteins. For example, the chimeric coding sequence can be modified to encode two or more neighboring histidine residues, for example, in the amino or carboxy terminus of the peptide. Histidine residue insertion can be readily accomplished by the splice-by-overlap extension methodology, by incorporating histidine-encoding CAT and CAC triplet codons into the PCR primers at suitable locations in the coding sequence. Histidine-modified proteins can be efficiently and quantitatively isolated by nickel-sepharose chromatography methods known in the art.

In some embodiments, therapeutics provided herein may also be conjugated to a second molecule, such as a therapeutic agent (e.g., a cytotoxic agent). For example, the therapeutic agent includes, but is not limited to, an anti-tumor drug, a toxin, a radioactive agent, a cytokine, a second antibody or an enzyme. Examples of cytotoxic agents include, but are not limited to ricin, ricin A-chain, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, maytansinoids, and glucocorticoid and other chemotherapeutic agents, as well as radioisotopes such as $^{212}$Bi, $^{131}$I, $^{90}$Y, and $^{186}$Re. Suitable detectable markers include, but are not limited to, a radioisotope, a fluorescent compound, a bioluminescent compound, chemiluminescent compound, a metal chelator or an enzyme. The therapeutics of the invention may also be conjugated to an anti-cancer pro-drug activating enzyme capable of converting the pro-drug to its active form. See, for example, U.S. Pat. No. 4,975, 287.

In some preferred embodiments, the secondary therapeutic agent has a complementary mode of action with the primary therapeutic agent. For example, in some embodiments, the primary and secondary therapeutic agents act against different aspects of a signal transduction system involved in the etiology of a cancer or other disease, leading to enhanced efficacy, fewer side effects, an improved therapeutic index, and/or other benefits relative to tailored therapeutics bearing the primary and/or secondary therapeutic agents only. In some embodiments, the first therapeutic agent potentiates the second therapeutic agent, or vice versa, or the first and second therapeutic agents exhibit a synergistic enhancement in one or more aspects of treatment. Methods for assessing synergism, potentiation, and other combined pharmacological effects are known in the art, and described, e.g., in Chou and Talalay, Adv Enzyme Regul., 22:27-55 (1984), incorporated herein by reference.

In some embodiments, the therapeutic agent is conjugated to an antibody immune effector component of the therapeutic. Techniques for conjugating or joining therapeutic agents to antibodies are well known (see, e.g., Arnon et al., "Monoclonal Antibodies For Immuno-targeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The therapeutics of the invention can be administered by any method known in the art that is suitable for protein pharmaceuticals, such as intravenous injection, intramuscular injection, topical administration, oral ingestion, rectal administration, and inhalation. Alternatively, the therapeutics of the present invention can be delivered directly to the site of the malignancy. The therapeutic may be administered in admixture with a pharmaceutically acceptable carrier. Any such carrier can be used according to the present methods, as long as compatibility problems do not arise. An effective amount of the present recombinant fusion protein should be administered to the patient. The term "effective amount" refers to that amount of the fusion protein needed to bring about the desired response.

Figure 8:
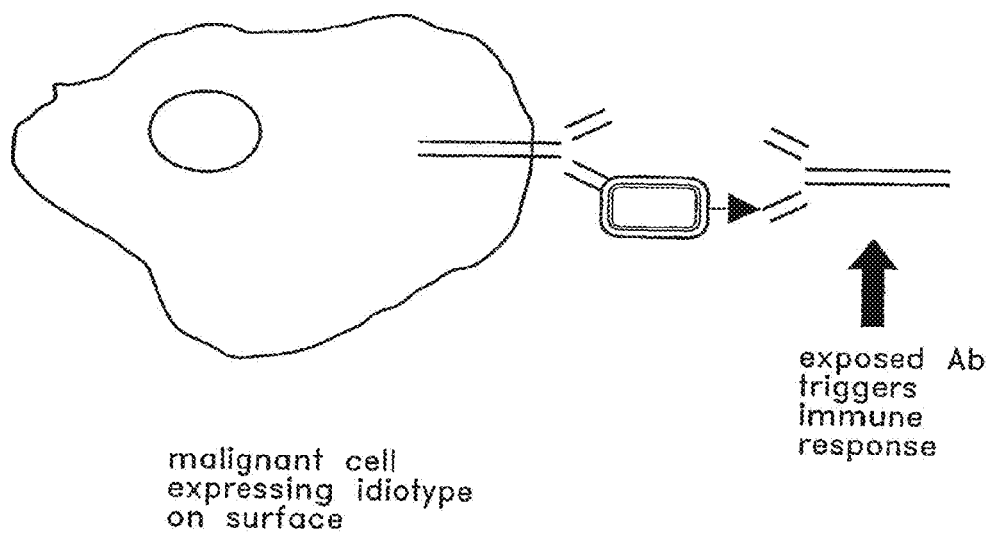

In some preferred embodiments, therapeutics made according to methods providing herein inhibit proliferation and/or induces apoptosis of cells bearing the epitope against which the epitope binding protein was screened. For example, in some embodiments, the epitope-binding portion of the therapeutic complex can bind with the epitopes expressed on the surface of malignant cells, or other targets. Once bound, the IR-eliciting antibody component of the complex stimulates the immune system to attack and eliminate the tagged cells, while sparing the normal cells, as illustrated in FIG. 8.

In various embodiments, the tailoring of individualized therapeutics provided herein for binding to patient- and/or disease-specific targets is made possible by utilizing novel methods for linking proteins to their corresponding mRNAs (as "cognate pairs"). In some preferred embodiments, protein libraries are prepared comprising a large number of cognate pairs, and the libraries are screened for cognate pairs that bind to a target of interest, such as the individualized targets described herein.

Figure 4:
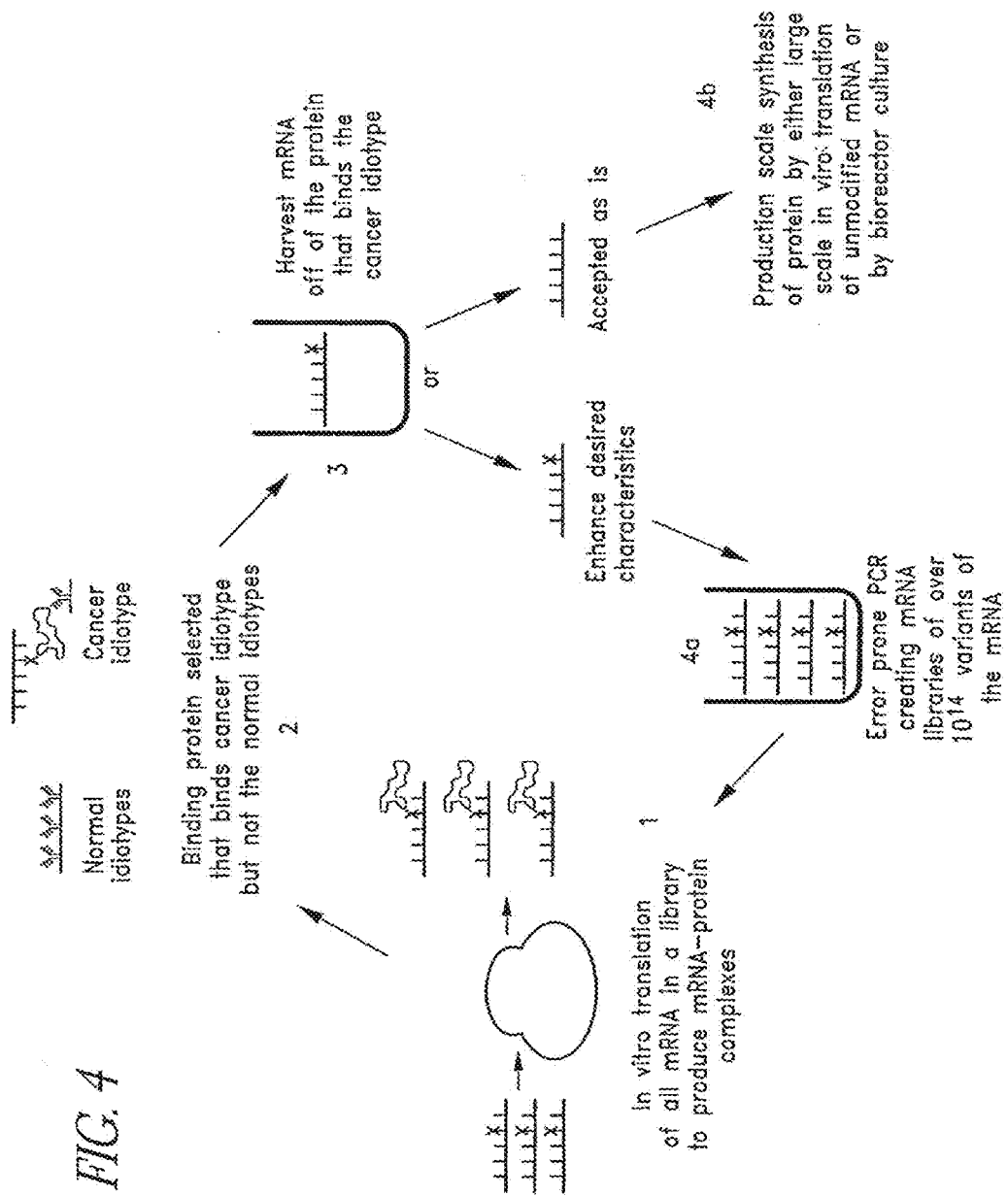

Various aspects of the present invention use modified tRNA and/or mRNA molecules to link translated protein products to their corresponding mRNAs via a tRNA linker, forming a "cognate pair." In several embodiments, mRNAs having unknown sequences are expressed in an in vitro translation system, for example from an mRNA library, and their corresponding proteins are screened for one or more desired characteristics, such as binding to the target epitope-binding domain, or another ligand of interest, and/or selectivity over one or more additional ligands, such as epitopes displayed by healthy cells. In further embodiments, proteins and their linked nucleic acids identified in one or more rounds of selection are modified, for example through nucleic acid evolution (FIG. 4), to produce proteins with enhanced affinities for the target ligand. Proteins having desired characteristics, such as a high affinity for the target ligand, can then be produced in large quantities using standard cloning techniques by isolating their corresponding mRNA from the protein-mRNA cognate pairs.

In some preferred embodiments, cognate pairs are formed using a eukaryotic in vitro translation system, such as rabbit reticulocyte lysate (RLL), wheat germ, E. coli, or yeast lysate systems. However, it is understood by the skilled artisan that any in vitro translation system can be used, including in situ systems, as well as hybrid systems, which combine components of different systems. For example, in some embodiments, one or more prokaryotic factors are used in a eukaryotic translation system, such as translation suppressor proteins (see e.g., Geller and Rich Nature 283:41 (1980); Edwards et al PNAS 88:1153 (1991); Hou and Schimmel Biochem 28:6800 (1989), all herein incorporated by reference). In some embodiments, one or more tRNAs or tRNA analogs are charged in a prokaryotic system and then purified according to established methods (Lucas-Lenard and Haenni, PNAS 63:93 (1969), herein incorporated by reference) for use in a eukaryotic system.

In various embodiments, proteins comprising cognate pairs are linked to tRNA or a tRNA analog by the action of ribosomal peptidyl transferase. In some embodiments, proteins are linked to a stable aminoacyl tRNA analog (SATA). In some embodiments, the SATA is a tRNA with an amino acid or amino acid analog attached to its 3' end via a stable bond, relative to the corresponding high-energy ester bond in the native structure. When the SATA recognizes a particular codon, for example via hydrogen bonding, and accepts a nascent peptide chain by the action of the ribosomal peptidyl transferase, the stable aminoacyl bond prevents the detachment of the tRNA from the polypeptide by peptidyl transferase, and also preserves the tRNA-polypeptide structure during subsequent steps.

In some embodiments, a SATA is created according to methods generally described in Fraser and Rich, PNAS, 70:2671 (1973), herein incorporated by reference, which involve the conversion of a tRNA, or tRNA analog, to a 3'-amino-3'-deoxy tRNA. This is accomplished by adding a 3'-amino-3'-deoxy adenosine to the end of a native tRNA with tRNA nucleotidyl transferase after removing the native adenosine, and then charging the modified tRNA with an amino acid with the respective aminoacyl tRNA synthetase (aaRS). In some embodiments, the aaRS charges the tRNA on the 3', rather than the 2', hydroxyl, linking the amino acid to the tRNA by a stable amide bond, rather than the usual labile high-energy ester bond. Thus, when the SATA accepts a peptide from ribosomal peptidyl transferase it will stably hold the peptide and be unable to donate it to another acceptor.

In certain embodiments, tRNAs aminoacylated via a 3' amide bond may not combine with the elongation factor EF-TU, which assists in binding to the A site (e.g., Sprinzl and Cramer, Prog. Nuc. Acid Res. 22:1 (1979), herein incorporated by reference). Such modified tRNAs do, however, bind to the A site. This binding of 3' modified tRNAs can be increased by changing the $Mg^{++}$ concentration (Chinali et al., Biochem. 13:3001 (1974), herein incorporated by reference). The appropriate concentrations of and/or molar ratios of SATA and $Mg^{2+}$ can be determined empirically. For example, if the concentration or A site avidity of a SATA is too high, the SATA may compete with native tRNAs for non-cognate codons, stalling translation. Alternatively, if the concentration or A site avidity of SATA is too low, the SATA might fail to effectively compete with release factors, preventing it from stably accepting the nascent peptide.

While the elongation factor is also believed to aid in proofreading codon-anticodon recognition, the absence of this source of proofreading would not be expected to interfere with methods provided herein. Without being bound to a particular mechanism, it is believed that the error rate in the absence of elongation factor and associated GTP hydrolysis is approximately 1 in 100 for codons one nucleotide away (Voet and Voet, Biochemistry $2^{nd}$ ed. pp. 1000-1002 (1995), John Wiley and Sons, herein incorporated by reference). In some preferred embodiments, UAA is used as the linking codon. UAA has 7 non stop codons that differ from it by one amino acid, which comprises 7/61, or about 11.5% of the non stop codons. Thus, the probability of miscoding a given codon can be estimated as $(0.01)(0.115)=1.15\times10^{-3}$ miscodes per codon, or about one miscode every 870 codons, a frequency that would not substantially impair performance of various methods described herein. In some additional embodiments, UAG can be used as the linking codon without substantial impairment due to the absence of elongation factor-mediated proofreading.

In one embodiment, the SATA is a tRNA, or tRNA analog, with one or more modified bases in the acceptor stem, or another region of the molecule. Various methods for producing tRNAs with acceptor stem modification are known in the art, and are described, for example, in Sprinzl and Cramer, Prog. Nuc. Acid Res., 22:1 (1979), herein incorporated by reference. In some embodiments, a tRNA is modified with a puromycin moiety, such that the tRNA mimics aminoacyl-Tyr tRNA and is incorporated into the nascent polypeptide, terminating translation. In some embodiments, acceptor stem-modified tRNAs are formed from "transcriptional tRNA", wherein the sequence of the tRNA itself, rather than post-transcriptional processing, leads to the atypical and modified bases. Transcriptional tRNAs are capable of functioning as tRNAs (see e.g., Dabrowski et al., EMBO J. 14:4872, 1995; and Harrington et al., Biochem. 32: 7617, 1993, both herein incorporated by reference). Transcriptional tRNA can be produced by methods known in the art, such as transcription, or by connecting commercially available RNA sequences (e.g., from Dharmacon Research Inc., Boulder, Colo.) together, piece-wise as in FIG. X, or by some combination of established methods. For example, with reference to Fig. X, the 5' phosphate and 3' puromycin are commercially available attached to oligoribonucleotides, which can be connected together using T4 DNA ligase (e.g., Moore and Sharp, Science 256: 992, (1992), herein incorporated by reference) or alternatively, T4 RNA ligase (Romaniuk and Uhlenbeck, Methods in Enzymology 100:52 (1983), herein incorporated by reference).

Additional methods for producing modified tRNAs are known in the art, and are described, e.g., in Chinali et al., Biochem. 13:3001 (1974) and Krayevsky and Kukhanova, Prog. Nuc. Acid Res 23:1 (1979), both herein incorporated by reference.

In some embodiments, the tRNA is a nonsense suppressor tRNA comprising a modified or unmodified tRNA, or tRNA analog, that recognizes a stop codon or a pseudo-stop codon, preferably by codon-anticodon hydrogen bonding, such that translation is terminated when the nascent protein is attached to the tRNA by peptidyl transferase. In some embodiments, the nonsense suppressor tRNA has 3' modifications and/or sequences that conform to the Yarus extended anticodon rules (Yarus, Science 218:646-652, 1982, herein incorporated by reference). A "pseudo stop codon," as defined herein, refers to a codon which, while not naturally a nonsense codon, prevents a message from being further translated. A pseudo stop codon can comprise a codon recognized by a "stable aminoacyl tRNA analog," or SATA, as described herein, or a codon for which tRNA bearing a complementary anticodon is substantially depleted or absent, such that translation is terminated when the absent tRNA is required, i.e. at the pseudo stop codon. One skilled in the art will appreciate that are numerous ways to create a pseudo stop codon, as defined herein.

In some preferred embodiments, the tRNA is a native tRNA, linked to the nascent polypeptide via a native peptide bond. In some embodiments, the SATA is a tRNA that is unmodified at the 3' end, but which may have one or more modifications to the anticodon loop and/or other regions of the molecule. In various embodiments, the use of native tRNAs and/or tRNAs that are unmodified at the 3' end results in improvements in various selection methods described herein, giving rise to quicker, less error-prone, more efficient, more cost-effective, and/or higher yield methods. While not being bound by a particular theory, it is believed that, under certain conditions, puromycin (and similar linkers) can result in lower yields due to interference with the interaction between elongation factor(s) and tRNAs.

In one embodiment of the invention, the crosslinker is an agent that chemically or mechanically links two molecules together. In one embodiment, the crosslinker is an agent that can be activated to form one or more covalent bonds with tRNA and/or mRNA. In one embodiment, the crosslinker is a sulfur-substituted nucleotide. In another embodiment, the crosslinker is a halogen-substituted nucleotide. Examples of crosslinkers include, but are not limited to, 2-thiocytosine, 2-thiouridine, 4-thiouridine, 5-iodocytosine, 5-iodouridine, 5-bromouridine and 2-chloroadenosine, aryl azides, and modifications or analogues thereof. In one embodiment, the crosslinker is psoralen or a psoralen analog.

Figure 3:
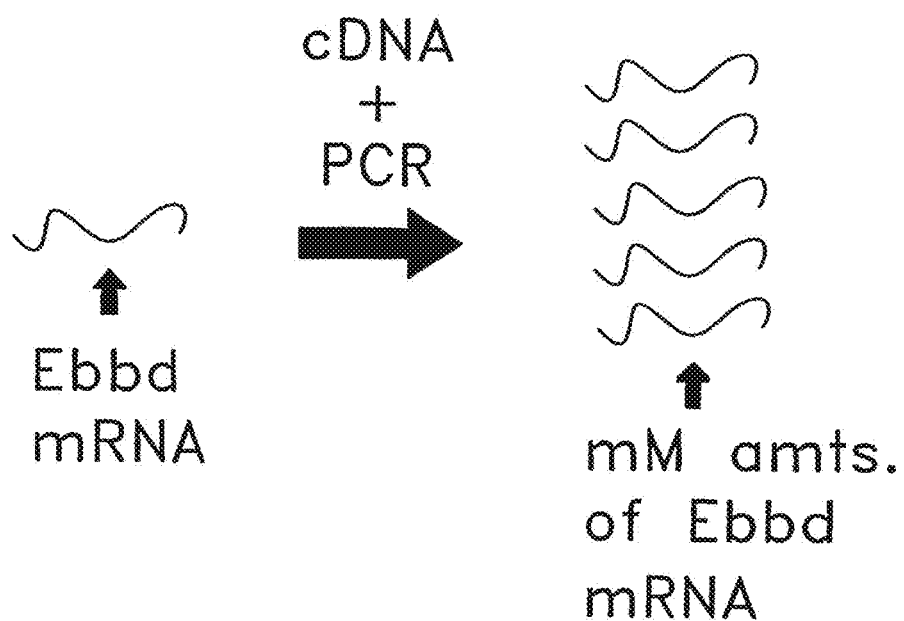
FIG. 3. Illustration of scaled up production of mRNA encoding an immune effector-binding protein (Ebbd) for ligation pur form a complete modified tRNA for use in the in vitro evolution methods of the invention. Other embodiments do not include puromycin.

In some preferred embodiments, a psoralen is monoadducted to a tRNA, or a tRNA analog (e.g., a 3' modified SATA), for example by connecting a psoralen linked oligonucleotide (FIG. 3), or by monoadduction (FIG. 4), to a native or modified tRNA or tRNA analog, preferably to the anticodon or another site distinct from the linkage to the polypeptide. When irradiated with UV light of a desired wavelength, a covalent psoralen crosslink is formed between the SATA and mRNA, as described in more detail below. In some embodiments, the anticodon or other portion of a tRNA is derivatized with a non-psoralen moiety capable of forming a crosslink to the mRNA, such as 2-thiocytosine, 2-thiouridine, 4-thiouridine 5-iodocytosine, 5-iodouridine, 5-bromouridine, 2-chloroadenosine, aryl azides, and modifications or analogues thereof. These and other cross-linkers are known in the art, and are available commercially, for example from Ambion, Inc. (Austin, Tex.), Dharmacon, Inc. (Lafayette, Colo.), and other well-known manufacturers of scientific materials.

In various embodiments, a SATA-polypeptide complex or a tRNA-polypeptide complex is linked to the mRNA encoding the polypeptide via a linker moiety, which can be located on the mRNA and/or on the tRNA. In some preferred embodiments, the mRNA comprises a cross-linker, preferably at or near a stop codon at the 3'-end of the transcript, and the mRNA-tRNA linkage is mediated entirely by the mRNA-based crosslinker. In further embodiments, the tRNA is unmodified at its 3'-end (e.g., a nonsense suppressor tRNA). In some preferred embodiments, an mRNA comprises a pseudo-stop codon located at the end of the translatable reading frame. A pseudo-stop codon can be effectively placed at the end of a reading frame where the pseudo-stop codon is located at the 3' end of the mRNA, where the translation system is depleted of tRNAs corresponding to codons 3' to the pseudo-stop codon, and/or where 3'-modified tRNAs corresponding to the pseudo-stop codon are used, rendering the transcript untranslatable and incapable of activating release factors. In some embodiments, the mRNA comprises a stop codon corresponding to a tRNA stop anticodon. Advantageously, a stop codon/anticodon pair selects for full-length transcripts. One skilled in the art will understand that an mRNA not having a stop codon may also be used and that any codon or nucleic acid triplet may be used.

In some methods, a SATA is attached to the translated message by a psoralen cross link between the codon and anticodon. Psoralen cross links are preferentially made between sequences that contain complementary 5' pyrimidine-purine 3' sequences, especially UA or TA sequences (Cimino et al., Ann. Rev. Biochem. 54:1151 (1985), herein incorporated by reference). The codon coding for the SATA, or the linking codon, can be PYR-PUR-X or X-PYR-PUR, so that several codons may be used for the linking codon. Conveniently, the stop or nonsense codons have this configuration. Using a codon that codes for an amino acid may require minor adjustments to the genetic code, which could complicate some applications. Therefore, in a preferred embodiment, a stop codon is used as the linking codon and the SATA functions as a nonsense suppressor in that it recognizes the linking codon. One skilled in the art, however, will appreciate that, with appropriate adjustments to the system, any codon can be used.

In some preferred embodiments, the SATA or peptidyl-tRNA is crosslinked to the translated mRNA, for example between the codon and anticodon, by a psoralen cross-link, or by a cross-link formed from the group consisting of: 2-thio cytosine, 2-thio uridine, 4thio uridine 5-iodocytosine, 5-iodouridine, 5-bromouridine, 2-chloroadenosine, and aryl azides. Psoralen cross links are, in some embodiments, preferentially made between sequences that contain complementary 5' pyrimidine-purine 3' sequences, especially UA or TA sequences (Cimino et al., Ann. Rev. Biochem. 54:1151 (1985), herein incorporated by reference). In some embodiments, non-psoralen crosslinkers or aryl azides are used and in certain embodiments, are particularly advantageous because they are less stringent in their requirements and therefore increase the possible codon-anticodon pairs.

In various embodiments, translation terminates when the nascent protein is attached to a SATA by the peptidyl transferase and/or when the end of the reading frame is reached. When a large number of ribosomes are in this position, the SATA and the mRNA are cross-linked by application of UV light. In a preferred method, cross-linking is accomplished by forming a psoralen crosslink upon irradiation with UV light, preferably in the range of 320 nm to 400 nm. Psoralens comprise a furan side and a pyrone side, and they readily intercalate between complementary base pairs in double stranded DNA, RNA, and DNA-RNA hybrids (Cimino et al., Ann. Rev. Biochem. 54:1151 (1985), herein incorporated by reference). In some preferred embodiments, psoralen cross-linking forms monoadducts, described more fully below, that are either pyrone sided or furan sided monoadducts. Upon further irradiation, the furan sided monoadducts can be covalently crosslinked to complementary base pairs, whereas the pyrone sided monoadducts cannot be further crosslinked. The formation of furan-sided psoralen monoadducts (MAf) is achieved according to established methods. In additional embodiments, psoralen can also be attached at the end of the reading frame of the message.

Methods for large scale production of purified MAf on oligonucleotides are described in the literature (e.g., Speilmann et al., PNAS 89:4514, 1992, herein incorporated by reference), as are methods that require less resources, but have some non-cross-linkable pyrone sided psoralen monoadduct contamination (e.g., U.S. Pat. No. 4,599,303; Gamper et al., J. Mol. Biol. 197:349 (1987); Gamper et al., Photochem. Photobiol. 40:29 (1984), both herein incorporated by reference). In several embodiments of the current invention, psoralen labeling is accomplished by using either method. In a preferred embodiment, furan sided monoadducts will be created using visible light, preferably in the range of approximately 400 nm-420 nm, according to the methods described in U.S. Pat. No. 5,462,733 and Gasparro et al., Photochem. Photobiol. 57:1007 (1993), both herein incorporated by reference. In one aspect of this invention, a SATA with a furan sided monoadduct or monoadducted oligonucleotides for placement on the 3' end of mRNAs, along with a nonadducted SATA are provided as the basis of a kit.

In one embodiment, the formation and reversal of monoadducts and crosslinks are performed according to the methods of Bachellerie et al. (Nuc Acids Res 9:2207 (1981)), herein incorporated by reference. In a preferred embodiment, efficient production of monoadducts, resulting in high yield of the end-product, is accomplished using the methods of Kobertz and Essigmann, J. A. Chem. Soc. 1997, 119, 5960-5961 and Kobertz and Essigmann, J. Org. Chem. 1997, 62, 2630-2632, both herein incorporated by reference.

Other methods for connecting the mRNA to its protein can be used, as well as methods of phage display.

In several embodiments, appropriate concentrations of SATA and $Mg^{++}$ are used in the in vitro translation system in the presence of the mRNA molecules, causing translation to cease when ribosomes reach a stop, or pseudo-stop, codon which permits the SATA to accept the peptide chain, as described above. After a short time, a substantial proportion and/or number of the stop or pseudo-stop codons are occupied by SATAs within ribosomes, and in some embodiments, the system is then irradiated with UV light to generate cross-links between the tRNA-polypeptides and their corresponding mRNAs. In several embodiments, the ribosomes are released or denatured after cross-linking of to mRNA, preferably by the depletion of $Mg^{++}$ through dialysis, dilution, or chelation. One skilled in the art will understand that other methods, including but not limited to, denaturation by changing the ionic strength, the pH, or the solvent system can also be used to release cognate pairs from associated ribosomes and/or other translation factors.

In various embodiments, cognate pairs are selected based on one or more desired characteristics. In some embodiments, the selection of cognate pairs is based upon the binding of a target cell, protein, and/or other biomolecule, as determined by any of a variety of established methods, including, but not limited to, arrays, affinity columns, immunoprecipitation, and the like. In some preferred embodiments, selection criteria are measured using a high throughput screening procedure. The selection can be positive or negative in various embodiments, according to the desired characteristics of the therapeutic agent. In several preferred embodiments, mRNAs whose sequences are unknown are expressed (e.g., in the form of an mRNA library from a patient, tissue, or other source of interest) and linked to their encoded polypeptides using methods described herein, and the cognate pairs are screened to select for desired properties. For example, in some preferred embodiments, cognate pairs are assayed for binding to a ligand of interest, such as an Fab idiotype displayed by a malignant cell, or other surface characteristic of a target cell. mRNA can be isolated for proteins exhibiting the desired binding characteristics, and large quantities of the protein can be produced using standard molecular cloning techniques known in the art. As described in more detail herein, the protein of interest can then be incorporated into a modular therapeutic agent, for example to target the agent to a patient- and/or disease-specific target.

In various embodiments, the selected cognate pairs can be those that do bind well to a ligand or those that do not. For instance, for a protein to accelerate a thermodynamically favorable reaction, i.e., act as an enzyme for that reaction, it should bind both the substrate and a transition state analog. However, the transition state analog should be bound much more tightly than the substrate. This is described by the equation $$\frac{k_{enzyme}}{k_{\varphi enzyme}} = \frac{K_{trans}}{K_{subst}}$$

where the ratio of the rate of the reaction with the enzyme, $k_{enzyme}$ to the rate without, $k_{enzyme}$, is equal to the ratio of the binding of the transition state to the enzyme $K_{trans}$ over the binding of the substrate to the enzyme $K_{subst}$ (Voet and Voet, Biochemistry $2^{nd}$ ed. p. 380, (1995), John Wiley.

In some preferred embodiments, proteins which compete poorly for binding to the substrate but compete well for binding to the transition state analog are selected. Operationally, this may be accomplished by taking the proteins that are easily eluted from a matrix with substrate or substrate analog bound to it and are the most difficult to remove from matrix with transition state analog bound to it. By sequentially repeating this selection and reproducing the proteins through replication and translation of the nucleic acid of the cognate pairs, an improved enzyme should evolve. Affinity to one entity and lack of affinity to another in the same selection process is used in several embodiments of the current invention. In some additional embodiments, cognate pairs can be selected according to one or more properties of the mRNA portion.

There are many methods known in the art for identifying epitopes expressed by normal and malignant cells. For example, in some embodiments, a peptide microarray can be used to isolate cell-specific marker peptides from a combinatorial library, as described, e.g., by Aina et al, "Therapeutic Cancer Targeting Peptides," Biopolymers 66:184-199 (2002). In some preferred embodiments, the protein-mRNA complex library is reacted an isolated population of malignant cells, and the degree of binding to the malignant cell epitope is measured relative to binding observed against a population of normal cells. In some embodiments, proteins are selected having substantial affinity for malignant cells, with substantially lower or no affinity for normal cells. For example, in some embodiments, polypeptides are identified that bind an epitope or other target of interest with an affinity of less than about 10 µM, preferably less than about 1 µM, more preferably less than about 0.1 µM, and even more preferably less than about 10 nM. In some preferred embodiments, a polypeptide has an affinity for the epitope or other target of less than about 1 nM. Screening methods can be carried out with the potential ligands (e.g., proteins linked to their cognate mRNA) and targets (e.g., cells targeted for treatment) in a variety of orientations. For example, in some embodiments, malignant cells are presented on a planar surface, such as a glass slide, and are exposed to a solution containing mRNA-protein cognate pairs. Bound proteins (cognate pairs) can be detected via a variety of methods known in the art. For example, in some embodiments, the cognate pairs are derivatized, preferably on the mRNA and/or the tRNA linker, with a detectable probe, such as a biotin moiety, which can then be detected with a secondary reporter probe, for example using avidin coated magnetic beads. The resultant idiotype-(protein:mRNA)-biotin-avidin-magnetic bead complex can be identified with a Ventana 320 automated immunohistochemistry system (Ventana Medical Systems, Tucson, Ariz.), or a similar system, as described, for example, in Davis et al., Clinical Cancer Research 5: 611-615, (1999).

The method can further comprise providing a plurality of distinct nucleic acid-polypeptide complexes, providing a ligand with a desired binding characteristic, contacting the complexes with the ligand, removing unbound complexes, and recovering complexes bound to the ligand.

Several methods of the current invention involve the evolution of nucleic acid molecules and/or proteins. In some embodiments, such methods comprise amplifying the nucleic acid component (as RNA, or corresponding cDNA) of the recovered complexes and introducing variation to the sequence of the nucleic acids, for example by error-prone PCR, as described, e.g., in Cadwell et al., PCR Methods Appl., 2: 28 (1992), incorporated herein by reference, in vitro recombination, described, e.g., in U.S. Pat. No. 5,605,793, mutagenesis, described, e.g., in U.S. Pat. No. 5,830,721, "DNA shuffling," described, e.g., in Coco et al., Nat Biotechnol, 19(4):354-9 (2001), and/or other methods known in the art. In some preferred embodiments, at least one amino acid substitution is introduced at each position in the protein. In further embodiments, the method further comprises translating polypeptides from the amplified and varied nucleic acids, linking them together using tRNA, and contacting them with the ligand to select another new population of bound complexes. Several embodiments of the present invention use selected protein-mRNA complexes in a process of in vitro evolution, especially the iterative process in which the selected mRNA is reproduced with variation, translated and again connected to cognate protein for selection.

The Replication Threshold

A nominal minimum number of replications for efficient evolution may be estimated using the following formulae. If there is a sequence which is n sequences in length, with a selective improvement r mutations away with a mutation rate of p, the probability of generating the selective improvement on replication may be determined as follows:

For r=1, probability of a mutation at the right point, p, times the probability that it mutated to the right one of the three nucleotides that are different from the starting point, ⅓, times the probability that the other n−1 sites remain unmutated, $(1-p)^{(n-r)}$, or $$P_r = \left(\frac{p}{3}\right)^1 (1-p)^{(n-1)}$$

where, P=the probability of attaining a given change r mutations away. More generally, for all r values:

$$P_r = \left(\frac{p}{3}\right)^r (1-p)^{(n-r)}$$

It is instructive to compare the chances of finding an advantage one mutation away with the chances three mutations away. This is because, given the triplet genetic code, any given codon can only change into nine other codons in one mutation. Indeed, it turns out that no codon can actually change into nine other amino acid codes in one mutation. The maximum number of amino acids that can be accessed in one mutation is seven amino acids and there are only eight codons of the sixty-four that can do this. Most codons have five or six out of nineteen other amino acids within one mutation. To reach all nineteen amino acids that are different from the starting one requires, in general, three mutations. These three mutations cannot be sequential since the two intervening ones will not, in general, be selectively advantageous. Therefore we need to use steps that are, at least, three mutations in size (r=3) to use all 20 amino acids.

For a mutation rate of 0.0067, which is that reported for "error-prone PCR", using a message of 300 nucleotides, which gives a short protein of 100 amino acids:

$$P_3 = 1.51 \times 10^{-9}$$

Therefore, one would expect to need a threshold of:

$$\frac{1}{1.51 \times 10^{-9}} = 6.64 \times 10^8$$

replications at that mutation rate to reasonably expect to reach the next amino acid that is advantageous. This is not the replication to use since the binomial expansion shows that over ⅓ of trials (actually about 1/e) would not contain the given sequence with selective advantage.

A poisson approximation for large n and small p for a given μ can be calculated so that we can compute the general term when n is, say, of the order $10^9$ and p is of the order $10^{-9}$. The general term of the approximation is:

$$\frac{\mu^r}{r! e^\mu}$$

An amplification factor of greater than approximately 6/P ensures that evolution will progress with the use of all amino acids. This is useful when the production of novel proteins precludes the use of "shuffling" of preexisting proteins.

Limits on Purification

Given a reversible binding where B and C compete for A:

$$AB \leftrightarrow A + B$$

$$AC \leftrightarrow A + C$$

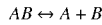

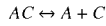

$$[B] = k_B \frac{[AB]}{[A]} \quad (1)$$

$$[C] = k_C \frac{[AC]}{[A]} \quad (2)$$

The total concentrations can be expressed as follows:

$$[B]_T = [B] + [AB] \quad (3)$$

$$[C]_T = [C] + [AC] \quad (4)$$

Dividing (3) by (4):

$$\frac{[B]_T}{[C]_T} = \frac{[B] + [AB]}{[C] + [AC]}$$

And substituting (1) and (2) for [B] and [C]:

$$\frac{[B]_T = k_B \left[\frac{AB}{A}\right] + [AB]}{[C]_T = k_C \left[\frac{AC}{A}\right] + [AC]}$$

Rearranging the equation gives the following results:

$$\frac{[B]_T}{[C]_T} = \frac{[AB]\left(\frac{k_B + [A]}{[A]}\right)}{[AC]\left(\frac{k_C + [A]}{[A]}\right)}$$

Canceling the [A]'s in the numerator and denominator:

$$\frac{[B]_T}{[C]_T} = \frac{[AB](k_B + [A])}{[AC](k_C + [A])}$$

Finally, rearranging the equation provides the following equation:

$$\frac{[AB]}{[AC]} = \frac{[B]_T(k_C + [A])}{[C]_T(k_B + [A])}$$

$$\frac{(k_C + [A])}{(k_B + [A])} \text{ (Enrichment Factor)}$$

The above factor is termed the "Enrichment Factor". The ratio of the total components is multiplied by this factor to calculate the ratio of the bound components, or the enrichment of B over C. The maximum enrichment factor is $k_c/k_B$, when the [A] is significantly smaller than $k_c$ or $k_B$. When [A] is significantly greater than $k_c$ or $k_B$, the enrichment is 1, that is, there is no enrichment of one over the other.

The enrichment is limited by the ratio of binding constants. To enrich a scarce protein that is bound 100 times as strongly as its competitors, the ratio of that protein to its competitors is increased by 1 million with 3 enrichments. To enrich a protein that only binds twice as strongly as its competitors, 10 enrichment cycles would gain only an enrichment of ~1000.

By an exactly analogous method an enrichment factor of selecting proteins that bind least well can be shown:

In the equation:

$$\frac{[C]}{[B]} = \frac{k_C[C]_T([A]+k_B)}{k_B[B]_T([A]+k_C)}$$

The enrichment here is maximal at $[A]>k_A$ or $k_B$.

$$\frac{k_C([A]+k_B)}{k_B([A]+k_C)}$$

The following Examples illustrate various embodiments of the present invention and are not intended in any way to limit the invention.

Example 1

Production of the SATA

One skilled in the art will understand that the SATA can be produced in a number of different ways. The protocols described below in the following examples can be used for SATAs that have both a puromycin and a crosslinker on the tRNA, or that have a puromycin on the tRNA and a crosslinker on the mRNA. Where the crosslinker is on the mRNA, Example 4, below, provides guidance. The following protocol is also instructive for Linking tRNA Analogs, in the sense that Linking tRNA Analogs also, in a preferred embodiments, have a crosslinker on the tRNA.

For example, in a preferred embodiment, three fragments (FIG. 1) were purchased from a commercial source (e.g., Dharmacon Research Inc., Boulder, Colo.). Modified bases and a fragment 3 with a pre-attached puromycin on its 3' end and a PO4 on its 3' end were included, all of which were available commercially. Three fragments were used to facilitate manipulation of the fragment 2 in forming the monoadduct.

Yeast tRNAAla or yeast tRNAPhe were used; however, sequences can be chosen from widely known tRNAs or by selecting sequences that will form into a tRNA-like structure. Preferably, sequences with only a limited number of U's in the portion that corresponds to the fragment 2 are used. Using a sequence with only a few U's is not necessary because psoralen preferentially binds 5'UA3' sequences (Thompson J. F., et al Biochemistry 21:1363, herein incorporated by reference). However, there would be less doubly adducted product to purify out if such a sequence was used.

Fragment 2 was preferably used in a helical conformation to induce the psoralen to intercalate. Accordingly, a complementary strand was required. RNA or DNA was used, and a sequence, such as poly C to one or both ends, was added to facilitate separation and removal after monoadduct formation was accomplished.

Fragment 2 and the cRNA were combined in buffered 50 mM NaCl solution. The Tm was measured by hyperchromicity changes. The two molecules were re-annealed and incubated for 1 hour with the selected psoralen at a temperature ~10° C. less than the Tm. The psoralen was selected based upon the sequence used. A relatively insoluble psoralen, such as 8 MOP, could be selected which has a higher sequence stringency but may need to be replenished. A more soluble psoralen, such as AMT, has less stringency but will fill most sites. Preferably, HMT is used. If a fragment 2 is chosen that contains more nontarget U's, a greater stringency is desired. Decreasing the temperature or increasing ionic strength by adding Mg++ was also used to increase the stringency. In a preferred embodiment, MG++ was omitted and ~400 mM NaCl solution was used.

Following incubation, psoralen was irradiated at a wavelength greater than approximately 400 nm. The irradiation depends on the wavelength chosen and the psoralen used. For instance, approximately 419 nm 20-150 J/cm2 was preferably used for HMT. This process results in an almost entirely furan sided monoadduct.

Purification of a Monoadduct

The monoadduct was then purified by HPLC as described in Sastry et al, J. Photochem. Photobiol. B Biol. 14:65-79, herein incorporated by reference. The fact that fragment 2 was separate from fragment 3 facilitated the purification step because, generally, purification of monoadducts ≥25 mer is difficult (Spielmann et al. PNAS 89: 4514-4518, herein incorporated by reference).

Ligation of Fragment 2 and 3

The fragment 2 was ligated to the fragment 3 using T4 RNA ligase. The puromycin on the 3' end acted as a protecting group. This is done as per Romaniuk and Uhlenbeck, Methods in Enzymology 100:52-59 (1983), herein incorporated by reference. Joining of fragment 2+3 to the 3' end of fragment 1 was done according to the methods described in Uhlenbeck, Biochemistry 24:2705-2712 (1985), herein incorporated by reference. Fragment 2+3 was 5' phosphorylated by polynucleotide kinase and the two half molecules were annealed.

In an alternative method, significant quantities of furan sided monoadducted U were formed by hybridizing poly UA to itself and irradiating as above. The poly UA was then enzymatically digested to yield furan sided U which was protected and incorporated into a tRNA analog by nucleoside phosphoramidite methods. Other methods of forming the psoralen monoadducts include the methods described in Gamper et al., J. Mol. Biol. 197: 349 (1987); Gamper et al., Photochem. Photobiol. 40:29, 1984; Sastry et al, J. Photochem. Photobiol. B Biol. 14:65-79; Spielmann et al. PNAS 89:4514-4518, U.S. Pat. No. 4,599,303, all herein incorporated by reference.

SATAs generated by the methods described above read UAG (anticodon CUA). Additionally, UAA or UGA was also used. In various embodiments, any message that had the stop codon that was selected as the "linking codon" was used.

Example 2

Production of Psoralenated Furan Sided Monoadducts

UV Light Exposure of RNA:DNA Hybrids

Equal volumes of 3 ng/ml RNA:cRNA hybrid segments and of 10 μg/ml HMT both comprised of 50 mM NaCl were transferred into a new 1.5 ml capped polypropylene microcentrifuge tube and incubated at 37° C. for 30 minutes in the dark. This was then transferred onto a new clean culture dish.

This was positioned in a photochemical reactor (419 nm peak Southern New England Ultraviolet Co.) at a distance of about 12.5 cm so that irradiance was ~6.5 mW/cm2 and irradiated for 60-120 minutes.

Removal of Low Molecular Weight Protoproducts

100 µl of chloroform-isoamyl alcohol (24:1) was pipetted and mixed by vortex. The mixture was centrifuged for 5 minutes at 15000×g in a microcentrifuge tube. The chloroform-isoamyl alcohol layer was removed with a micropipette. The chloroform-isoamyl alcohol extraction was repeated once again. Clean RNA was precipitated out of the solution.

Alcohol Precipitation

Two volumes (~1000 µl) ice cold absolute ethanol was added to the mixture. The tube was centrifuged for 15 minutes at 15,000×g in a microcentrifuge. The supernatant was decanted and discarded and the precipitated RNA was redissolved in 100 µl DEPC treated water then re-exposed to the RNA+8-MOP.

Isolation of the Psoralenated RNA Fragments Using HPLC

All components, glassware and reagents were prepared so that they were RNAase free. The HPLC was set up with a Dionex DNA PA-100 package column. The psoralenated RNA:DNA hybrid was warmed to 4° C. The psoralenated RNA was applied to HPLC followed by oligonucleotide analysis, as described in the following section entitled "Oligonucleotide Analysis by HPLC." The collected fractions represented:

```
                                            (SEQ ID NO: 1)
5'CUAGAΨCUGGAGG3', where Ψ is pseudouridine (SEQ ID NO: 2)
Furan sided 5'CUPsoralenAGAΨCUGGAGG3' monoadducts (SEQ ID NO: 3)
5'XXXXXCCUCCAGAUCUAGXXXXX3'

(SEQ ID NO: 4)
5'XXXXXCCUCCAGAUCUPsoralenAGXXXXX3'
```

The fractions were stored at 4° C. in new, RNAase free snapped microcentrifuge tubes and stored at −20° C. if more than four weeks of storage were required.

Identification of the RNA Fragments Represented by Each Peak Fraction Collected by HPLC Using Polyacrylamide Gel Electrophoresis (PAGE)

The electrophoresis unit was set up in a 4° C. refrigerator. A gel was selected with a 2 mm spacer. Each 5 µl of HPLC fraction was diluted to 10 µl with Loading Buffer. 10 µl of each diluted fraction was loaded into appropriately labeled sample wells. The tracking dye was loaded in a separate lane and electrophoresis was run as described in the following section entitled "Polyacrylamide Gel Electrophoresis (PAGE) of Psoralenated RNA Fragments." After the electrophoresis run was complete, the electrophoresis was stopped when the tracking dye reached the edge of the gel. The apparatus was disassembled. The gel-glass panel unit was placed on the UV light box. UV lights were turned on. The RNA bands were identified. The bands appeared as denser shadows under UV lighting conditions.

Extraction of the RNA From the Gel

Each band was excised with a new sterile and RNAase free scalpel blade and transferred into a new 1.5 ml snap capped microcentrifuge tube. Each gel was crushed against the walls of the microcentrifuge tubes with the side of the scalpel blade. A new blade was used for each sample. 1.0 ml of 0.3M sodium acetate was added to each tube and eluted for at least 24 hours at 4° C. The eluate was transferred to a new 0.5 ml snap capped polypropylene microcentrifuge tube with a micropipette. A new RNAase free pipette tip was used for each tube and the RNA with ethanol was precipitated out.

Ethanol Precipitation

Two volumes of ice cold ethanol was added to each eluate then centrifuged at 15,000×g for 15 minutes in a microcentrifuge. The supernatants were discharged and the precipitated RNA was re-dissolved in 100 µl of DEPC treated DI water. The RNA was stored in the microcentrifuge tubes at 4° C. until needed. The tubes were stored at −20° C. if storage was for more than two weeks. The following was order of rate of migration for each fragment in order from fastest to slowest:

```
                                            (SEQ ID NO: 1)
5'CUAGAΨCUGGAGG3'

(SEQ ID NO: 2)
Furan sided 5'CUPsoralenAGAΨCUGGAGG3' monoadducts (SEQ ID NO: 3)
5'XXXXXCCUCCAGAUCUAGXXXXX3'

(SEQ ID NO: 4)
5'XXXXXCCUCCAGAUCUPsoralenAGXXXXX3'
```

The tubes containing the remainder of each fraction were labeled and stored at −20° C.

Ethanol Precipitation

RNA oligonucleotide fragments were precipitated, and all glassware was cleaned to remove any traces of RNase as described in the following section entitled "Inactivation of RNases on Equipment, Supplies, and in Solutions." All solutions were stored in RNAase free glassware and introduction of nucleases was prevented. Absolute ethanol was stored at 0° C. until used. Micropipettes were used to add two volumes of ice cold ethanol to nucleic acids that were to be precipitated in microcentrifuge tubes. Capped microcentrifuge tubes were placed into the microfuge and spun at 15,000×g for 15 minutes. The supernatant was discarded and precipitated RNA was re-dissolved in DEPC treated DI-water. RNA was stored at 4° C. in microcentrifuge tubes until ready to use.

Ligation of RNA Fragments 2 and 3

All glassware was cleaned to remove any traces of RNase as described in the following section entitled "Inactivation of RNases on Equipment, Supplies, and in Solutions." The following was added to a new 1.5 ml polypropylene snap capped microcentrifuge tube using a 100-1000 µl pipette and a new sterile pipette tip was used for each solution:

| Fragment 2 (3.0 nM) | 125.00 µl |
| Fragment 3 (3.0 nM) | 125.00 µl |
| Reaction buffer | 250.00 µl |
| RNA T4 ligase (9-12 U/ml) | 420 µl |

Reaction Buffer

| RNase free DI-water | 90.00 ml |
| Tris-HCl (50 mM) | 0.79 g |
| MgCl2 (10 mM) | 0.20 g |
| DTT (5 mM) | 0.078 g |
| ATP (1 mM) | 0.55 g |
| pH to 7.8 with HCL | |
| RNase free DI-water | QS to 100.00 ml |

The mixture was gently mixed and the RNA was melted by incubating the mixture at 16° C. for one hour in a temperature controlled refrigerated chamber. RNA was precipitated out of the solution immediately after the incubation was completed.

Alcohol Precipitation

Two volumes (~1000 μl) of ice cold absolute ethanol were added to the reaction mixture. The microcentrifuge tube was placed in a microcentrifuge at 15,000×g for 15 minutes. The supernatant was decanted and discarded and the precipitated RNA was re-dissolved in 100 μl DEPC treated water. The mixture was electrophoresed as described in the following section entitled "Polyacrylamide Gel Electrophoresis (PAGE) of Psoralenated RNA Fragments." The following was the order of rate of migration for each fragment in order from fastest to slowest:

a) Frag. 2
(SEQ ID NO: 5)
5'CUAGAΨCUGGAGG3'-OHPsoralen b) Frag. 3
(SEQ ID NO: 6)
5'UCCUGUGTΨCGAUCCACAGAAUUCGCACC-Puromycin c) Frag 2 + 3
(SEQ ID NO: 7)
5'CUPsoralenAGAYCUGGAGGUCCUGUGTΨCGAUCCACAGAA UUCGCACC Puromycin Each fraction was isolated by UV shadowing, the bands were cut out, the RNAs were eluted from the gels and the RNA elute was precipitated out as described in the following section entitled "Polyacrylamide Gel Electrophoresis (PAGE) of Psoralenated RNA Fragments." The ligation procedure was repeated with any residual unligated fragment 2 and 3 fractions. The ligated fractions 2 and 3 were pooled and stored in a small volume of RNase free DI-water at 4° C.

Ligation of RNA Fragment 1 with Fragment 2+3

All glassware was cleaned to remove any traces of RNase as described in the following section entitled "Inactivation of RNases on Equipment, Supplies, and in Solutions." The following was added to a new 1.5 ml polypropylene snap capped microcentrifuge tube. A 100-1000 μl pipette and new tip was used for each solution:

| Fragment 2 + 3 (3.0 nM) | 125.0 μl |
| Reaction buffer | 250.0 μl |
| T4 Polynucleotide Kinase(5-10 U/ml) | 1.7 μl |

Reaction Buffer

| RNase free DI-water | 90.00 ml |
| Tris-HCl (40 mM) | 0.63 g |
| MgCl2 (10 mM) | 0.20 g |
| DTT (5 mM) | 0.08 g |
| ATP (1 mM) | 0.006 g |
| pH to 7.8 with HCL | |
| RNase free DI-water | QS to 100.00 ml |

The RNA was gently mixed then melted by heating the mixture to 70° C. for 5 minutes in a heating block. The mixture was cooled to room temperature over a two hour period and the RNA was allowed to anneal in a tRNA configuration. The RNA was precipitated out of the solution.

Alcohol Precipitation

Two volumes (~1000 μl) of ice cold absolute ethanol were added to the reaction mixture. The microcentrifuge tube was placed in a microcentrifuge at 15,000×g for 15 minutes. The supernatant was decanted and discarded and the precipitated RNA was re-dissolved in 100 μl DEPC treated water. The mixture was electrophoresed as described in the following section entitled "Polyacrylamide Gel Electrophoresis (PAGE) of Psoralenated RNA Fragments." The following was the order of rate of migration for each fragment in order from fastest to slowest:

a) Frag. 1
(SEQ ID NO: 8)
5'GCGGAUUUAGCUCAGUUGGGAGAGCGCCAGACU3' b) Frag 2 + 3
(SEQ ID NO: 6)
5'CUPsoralenAGAYCUGGAGGUCCUGUGTΨCGAUCCACAGAA

UUCGCACCPuromycin c) Frag. 1 + 2 + 3
(SEQ ID NO: 9)
5'GCGGAUUUAGCUCAGUUGGGAGAGCGCCAGACUCUPsoral enAGAΨCUGGAGGUCCUGUGTTCGAUCCACAGAAUUCGCACC Puromycin Each fraction was isolated by UV shadowing, the bands were cut out, the RNAs were eluted from the gels and the RNA elute was precipitated out as described in the following section entitled "Polyacrylamide Gel Electrophoresis (PAGE) of Psoralenated RNA Fragments." The ligation procedure was repeated with the unligated Fragment 1 and the 2+3 Fraction. The ligated fractions 2+3 were pooled and stored in a small volume of RNase free DI-water at 4° C.

Final RNA Ligation

The following was added to a new 1.5 ml polypropylene snap capped microcentrifuge tube. A 100-1000 μl pipette and new tip was used for each solution:

| Fragment 1 + 2 + 3 (3.0 nM) | 250 μl |
| reaction buffer | 250 μl |
| RNA T4 ligase (44 μg/ml) | 22 μg |

The mixture was incubated at 17° C. in a temperature controlled refrigerator for 4.7 hours. Immediately after the incubation the tRNA was precipitated out as described in step 6.2 above and the tRNA was isolated by electrophoresis as described in the following section entitled "Polyacrylamide Gel Electrophoresis (PAGE) of Psoralenated RNA Fragments." The tRNA was pooled in a small volume of RNase free water and stored at 4° C. for up to two weeks or stored at −20° C. for periods longer than two weeks.

Polyacrylamide Gel Electrophoresis (PAGE) of Psoralenated RNA Fragments

Acrylamide Gel Preparation

All reagents and glassware were made RNAase free as described in the following section entitled "Inactivation of RNases on Equipment, Supplies, and in Solutions." The gel apparatus was assembled to produce a 4 mm thick by 20 cm×42 cm square gel. 29 parts acrylamide with 1 part ammonium crosslinker were mixed at room temperature with the appropriate amount of acrylamide solution in an RNAase free, thick walled Erlenmeyer flask.

Acrylamide Solution

| urea (7M) | 420.42 g |
| TBE (1X) | QS to 1 L |

5×TBE

| | |
|---|---|
| 0.455M Tris-HCl | 53.9 g |
| 10 mM EDTA | 20 ml of 0.5M |
| RNAase free DI water | 900 ml |
| pH with boric acid to | pH 9 |
| QS with RNAase free DI water to | 1 L |

The mixture was degassed with vacuum pressure for one minute. The appropriate amount of TEMED was added, mixed gently, and then the gel mixture was poured between the glass plates to within 0.5 cm of the top. The comb was immediately inserted between the glass sheets and into the gel mixture. An RNAase free gel comb was used. The comb produced wells for a 5 mm wide dye lane and 135 mm sample lanes. The gel was allowed to polymerize for about 30-40 minutes then the comb was carefully removed. The sample wells were rinsed out with a running buffer using a micropipette with a new pipette tip. The wells were then filled with running buffer.

Sample Preparation

An aliquot of the sample was suspended in loading buffer in a snap capped microcentrifuge tube and vortex mixed. Indicator dye was not added to the sample.

Loading Buffer

| | |
|---|---|
| Urea (7M) | 420.42 g |
| Tris HCl (50 mM) | 7.85 g |
| QS with RNAase free D-H2O | to 1 L |

Electrophoresis Run

The maximum volume of RNA/loading buffer solution was loaded into the 135 mm sample wells and the appropriate volume of tracking dye in 5 mm tracking lane. The samples were electrophoresed in a 5° C. refrigerator. The electrophoresis was stopped when the tracking dye reached the edge of the gel. The apparatus was then disassembled. Glass panels were not removed from the gel. The gel-glass panel unit was placed on a UV light box. With UV filtering goggles in place, the UV lights were turned on. The RNA bands were identified. They appeared as denser shadows under UV lighting conditions. The RNA was extracted from the gel. Each band was excised with a new sterile and RNAase free scalpel blade and each band was transferred into a new 1.5 ml snap capped microcentrifuge tube. Each gel was crushed against the walls of the microcentrifuge tubes with the side of the scalpel blade. A new blade was used for each sample. 1.0 ml of 0.3M sodium acetate was added to each tube and eluted for at least 24 hours at 4° C. The eluate was transferred to a new 0.5 ml snap capped polypropylene microcentrifuge tubes with a micropipette with a new RNAase free pipette tip for each tube. Two volumes of ice cold ethanol was added to each eluate, then centrifuged at 15,000×g for 15 minutes in a microcentrifuge. The supernatants were discarded and the precipitated RNA was redissolved in 100 µl of DEPC treated DI water. The RNA was stored in the microcentrifuge tubes at 4° C. until needed.

Oligonucleotide Analysis By HPLC

HPLC purification of the RNA oligonucleotides is best effected using anion exchange chromatography. Either the 2'-protected or 2'-deprotected forms can be chromatographed. The 2'-protected form offers the advantage of minimizing secondary structure effects and provides resistance to nucleases. If the RNA is fully deprotected, sterile conditions are required during purification.

Deprotection of 2'-Orthoester Protected RNA

The tubes are centrifuged at 15,000×g for 30 seconds or until the RNA pellet is at the bottom. 400 µl of pH 3.8 deprotection buffer is added to each tube of RNA.

Deprotection Buffer

Acetic acid (100 mM) is adjusted to pH 3.8 with tetramethylethylenediamine (TEMED). The pellet is completely dissolved in the buffer by drawing in and out of a pipette. The tubes are vortexed for 10 seconds and centrifuged at 15,000× g. The tubes are incubated in a 60° C. water bath for 30 minutes. The samples are lyophilized before use.

HPLC Column Conditions

A 4×250 mm column (DNAPAC PA, No. 043010) packed with Dionex (800)-DIONEX-0 (346-6390), with a capacity of 40 optical density units (ODU) at 260 nm is installed. The column temperature is set to 54° C. The injection volume is adjusted such that 5 µl produces approximately 0.20 ODU.

Elution Buffers

| Condition | Buffer A | Buffer B |
|---|---|---|
| Sodium perchlorate | (5 mM) 2.8 g | (300 mM)168.0 g |
| Tris-HCl | 2.4 g | 2.4 g |
| Acetonitrile (2%) | 80.0 ml | 80.0 ml |
| DI Water | 3900 ml | 900 ml |
| Adjusted pH | 8.0 with HCL | 8.0 with HCL |
| q.s. | 4000 ml | 4000 ml |

HPLC Gradient

A 30% to 60% gradient of Buffer B for oligos 17-32 base pairs long is provided:

| Time (minutes) | Flow (ml/min) | % A | % B | Curve |
|---|---|---|---|---|
| 0 | 1.5 | 100 | 0 | * |
| 1 | 1.5 | 100 | 0 | 6 |
| 3 | 1.5 | 70 * | 30 * | 6 |
| 15 | 1.5 | 40 * | 60 * | 6 |
| 15.5 | 2.5 | 0 | 100 | 6 |
| 17 | 2.5 | 0 | 100 | 6 |
| 17.25 | 2.5 | 100 | 0 | 6 |
| 23 | 2.5 | 100 | 0 | 6 |
| 23.1 | 1.5 | 100 | 0 | 6 |
| 24 | 1.5 | 100 | 0 | 6 |
| 25 | 0.1 | 100 | 0 | 6 |

* % values that can be changed to modify the gradient. Typical gradients are 0-30%, 20-50%, 30-60%, and 40-70% of Buffer B.

Gradient Selection

The gradient is selected based upon the number of bases, as follows:

| Number of bases | Gradient |
|---|---|
| 0-5 | 0-30 |
| 6-10 | 10-40 |
| 11-16 | 20-50 |
| 17-32 | 30-60 |
| 33-50 | 40-70 |
| >50 | 50-80 |

After HPLC, the target samples are collected and the RNA concentration is determined with a spectrophotometer at 260 nm. The samples are stored at −70° C.

Inactivation of RNAses on Equipment, Supplies, and in Solutions

Glassware was treated by baking at 180° C. for at least 8 hours. Plasticware was treated by rinsing with chloroform. Alternatively, all items were soaked in 0.1% DEPC.

Treatment with 0.1% DEPC 0.1% DEPC was prepared. DI water was filtered through a 0.2 μM membrane filter. The water was autoclaved at 15 psi for 15 minutes on a liquid cycle. 1.0 g (wt/v) DEPC/liter of sterile filtered water was added.

Glass and Plasticware

All glass and plasticware was submerged in 0.1% DEPC for two hours at 37° C. The glassware was rinsed at least 5× with sterile DI water. The glassware was heated to 100° C. for 15 minutes or autoclaved for 15 minutes at 15 psi on a liquid cycle.

Electrophoresis Tanks Used for Electrophoresis of RNA

Tanks were washed with detergent, rinsed with water then ethanol and air dried. The tank was filled with 3% (v/v) hydrogen peroxide (30 ml/L) and left standing for 10 minutes at room temperature. The tank was rinsed at least 5 times with DEPC treated water.

Solutions

All solutions were made using Rnase free glassware, plastic ware, autoclaved water, chemicals reserved for work with RNA and RNase free spatulas. Disposable gloves were used. When possible, the solutions were treated with 0.1% DEPC for at least 12 hours at 37° C. and then heated to 100° C. for 15 minutes or autoclaved for 15 minutes at 15 psi on a liquid cycle.

RNA Translation

2 μl of gastroinhibitory peptide (GIP) mRNA at a concentration of 20 μl/ml was placed in a 250 μl snapcap polypropylene microcentrifuge tube. 35 μl of rabbit reticulocyte lysate (available commercially from Promega) was added. 1 μl of amino acid mixture which did not contain methionine (available commercially from Promega) was added. 1 μl of $^{35}$S methionine or unlabeled methionine was added. 2 μl of $^{32}$P GIP mRNA or unlabeled GIP mRNA was added. Optionally, 2 ml of luciferase may be added to some tubes to serve as a control. In a preferred embodiment, luciferase was used instead of GIP mRNA. One skilled in the art will understand that indeed any mRNA fragment containing the appropriate sequences may be used.

SATA was added to the experimental tubes. Control tubes which did not contain SATA were also prepared. The quantity of SATA used was approximately between 0.1 μg to 500 μg, preferably between 0.5 μg to 50 μg. 1 μl of Rnasin at 40 units/ml was added. Nuclease free water was added to make a total volume of 50 μl.

For proteins greater than approximately 150 amino acids, the amount of tRNA may need to be supplemented. For example, approximately 10-200 μg of tRNA may be added. In general, the quantity of the SATA should be high enough to effectively suppress stop or pseudo stop codons. The quantity of the native tRNA must be high enough to out compete the SATA which does not undergo dynamic proofreading under the action of elongation factors.

Each tube was immediately capped, parafilmed and incubated for the translation reactions at 30° C. for 90 minutes. The contents of each reaction tube was transferred into a 50 μl quartz capillary tube by capillary action. The SATA was crosslinked with mRNA by illuminating the contents of each tube with 2-10 J/cm2~350 nm wavelength light, as per Gasparro et al. (Photochem. Photobiol. 57:1007 (1993), herein incorporated by reference). Following photocrosslinking, the contents of each tube were transferred into a new snapcap microfuge tube. The ribosomes were dissociated by chelating the calcium cations by adding 2 μl of 10 mM EDTA to each tube. Between each step, each tube was gently mixed by stirring each component with a pipette tip upon addition.

The optimal RNA for a translation was determined prior to performing definitive experiments. Serial dilutions may be required to find the optimal concentration of mRNA between 5-20 μg/ml.

SDS-Page electrophoresis was performed on each sample, as described above. Autoradiography on the gel was performed, as described by Sambrook et. al., Molecular Cloning, A Laboratory Manual, $2^{nd}$ ed., Coldspring Harbor Press (1989), herein incorporated by reference.

The above example teaches the production and use of SATA (e.g., puromycin on tRNA plus crosslinker on the tRNA) and the production and use of Linking tRNA Analog (e.g., no puromycin, but has crosslinker on tRNA).

In another example, the SATA was produced in a manner similar to the above methodology, except that uridines were substituted with pseudouridines. Substitution by pseudouridines can also be used with Linking tRNA Analog, as it facilities the formation of crosslinker monoadduct formation (such as formation of the psoralen monoadduct). This technique is discussed below in Example 2.

Example 3

Production of the SATA Using Pseudouridine

Figure 5:
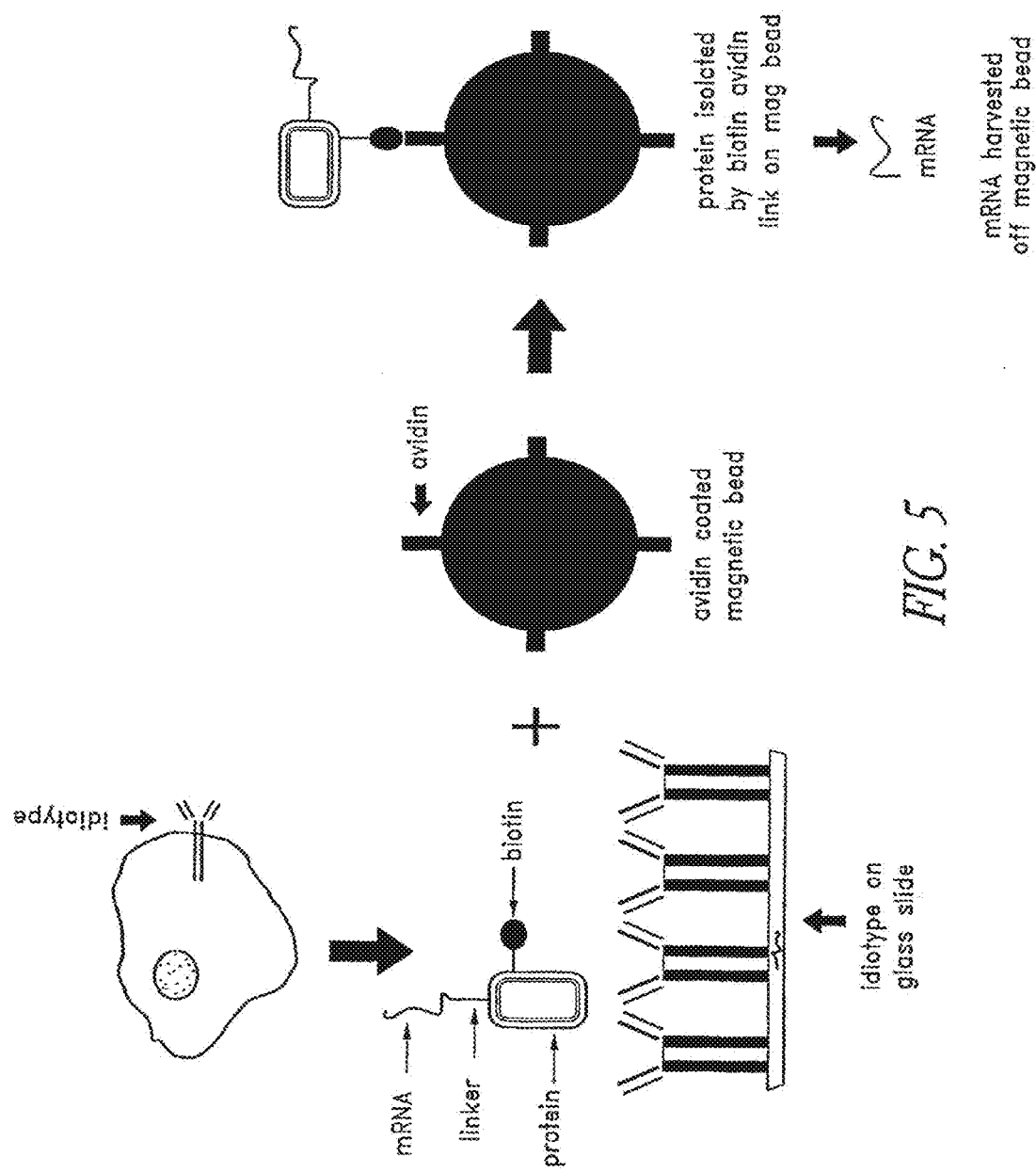
Figure 6:
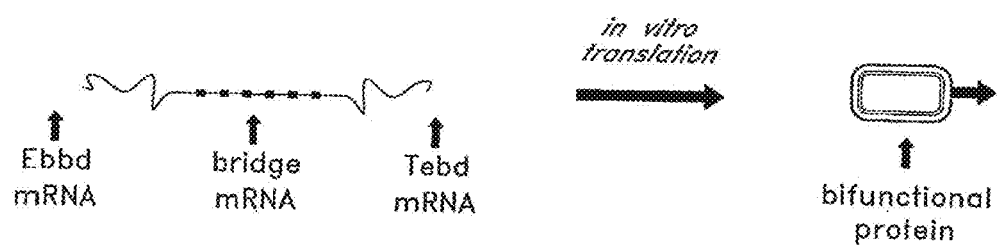
Figure 7:
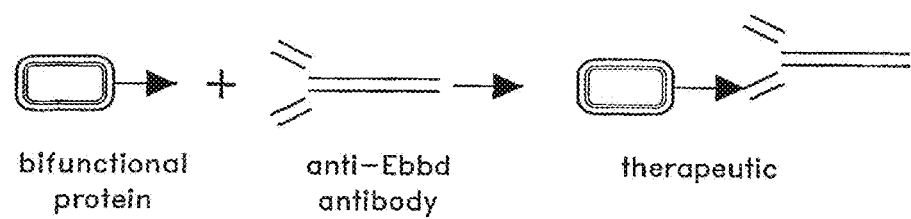

As discussed above, one skilled in the art will appreciate that the SATA, Linking tRNA Analog and Nonsense Suppressor tRNA can be produced in a number of different ways. FIG. 5 shows the chemical structures for uridine and pseudouridine. Pseudouridine is a naturally occurring base found in tRNA that forms hydrogen bonds just as uridine does, but lacks the 5-6 double bond that is the target for psoralen. Pseudouridine, as used herein, shall include the naturally occurring base and any synthetic analogs or modifications. In a preferred embodiment, the SATA was produced using pseudouridine. Linking tRNA Analog can also be produced using pseudouridine. Specifically, in a preferred embodiment, three fragments (FIG. 1) were purchased from a commercial source (Dharmacon Research Inc., Boulder, Colo.). Modified bases and a fragment 3 ("Fragment 3") with a pre-attached puromycin on its 3' end and a $PO_4$ on its 3' end were included, all of which are available commercially. The three fragments were used to facilitate manipulation of a fragment 2 ("Fragment 2") in forming the monoadduct. Sequences of the three fragments, according to some embodiments, are as follows (2 example sequences are provided for each fragment):

```
Fragment 1
5'PO4GCGGAUUUAGCUCAGUUGGGAGAGCGCCAGACOH3'           (SEQ ID NO: 10)

5'PO4GCGGAUUUAGCUCAGUUGGGAGAGCGCCAGACOH3'           (SEQ ID NO: 16)

Fragment 2
5'OHΨCUAACΨCOH3'                                     (SEQ ID NO: 11)

5' OHΨCUAAAΨCOH 3'                                   (SEQ ID NO: 17)
```

```
Fragment 3
5'PO4UGGAGGUCCUGUGTΨCGAUCCACAGAAUUCGCACCPuromycin3'  (SEQ ID NO: 12)

5'PO4UGGAGGUCCUGUGTΨCGAUCCACAGAAUUCGCACCPuromycin3'  (SEQ ID NO: 18)
```

The above sequences listed in Fragment 3 are applicable for SATA. For Linking tRNA Analogs, the sequences would be similar, except the puromycin would be replaced by adenosine.

Modified yeast tRNAAla or yeast tRNAPhe was used according to one embodiment of the invention. However, one skilled in the art will understand that sequences can be chosen widely from known tRNAs or by selecting sequences that will form into a tRNA-like structure. One advantage of using pseudouridine in some embodiments is that the pseudouridine in Fragment 2 avoids psoralen labeling of the nontarget U's. Use of pseudouridine instead of uridine decreases the avidity of the A site of the ribosome for the tRNA analog but eliminates the interaction of the terminal uridine with psoralen. The use of the Yarus "extended anticodon" guidelines increases A site binding (Yarus, Science 218:646-652, 1982, herein incorporated by reference).

In one embodiment, Fragment 2 was used in a helical conformation to induce the psoralen to intercalate. One skilled in the art will understand that other conformations can also be used in accordance with several embodiments of the invention. A complementary strand was also used. RNA or DNA was used, and a sequence, such as poly C or poly G when C interacts with the psoralen to one or both ends, was added to facilitate separation and removal after monoadduct formation was accomplished. Use of pseudouridine instead of uridines in the complement permitted the use of a high efficiency wave length, such as about 365 nm, without fear of crosslinking the product. Irradiation was preferably in the range of about 300-450 nm, more preferably in the range of about 320 to 400 nm, and most preferably about 365 nm. Further, use of pseudouridine left the furan-sided monoadduct in place on Fragment 2 because the Maf is the predominate first step in the crosslink formation.

The following cRNA sequences with pseudouridine were used according to a preferred embodiment of the present invention. One skilled in the art will understand that substitutions and modifications of these sequences, and of the other sequences listed herein, can also be used in accordance with several embodiments of the current invention. For example, for SEQ ID NO: 19, listed below, the sequence can also be

```
5'XXXXXXGAΨΨΨAGAXXXXXXX3':    (SEQ ID NO: 30)

CCCΨCCAGAGΨΨAGACCC            (SEQ ID NO: 13)

5'CCCCCCGAΨΨΨAGACCCCCCC3'     (SEQ ID NO: 19)
```

Step 1: Furan Sided Monoadduction of Psoralen to Fragment 2

The formation of a furan sided psoralen monoadduct with the target uridine of Fragment 2 was performed as follows:
A reaction buffer was prepared as follows:

| | |
|---|---|
| Tris HCL | 25 mM |
| NaCl | 100 mM |
| EDTA | 0.32 mM |
| pH | 7.0 |

4'hydroxy methyl-4,5',8'-triethyl psoralen (HMT) was then added to a final concentration of 0.32 mM and equimolar amounts of fragment 2 and cRNA were added to a final molar ratio of fragment 2:cRNA:psoralen=1:1:1000. A total volume of 100 µl was irradiated at a time.

The mixture of complementary oligos, HMT, psoralen was processed as follows:
1) Heated to 85° C. for 60 sec followed by cooling to 4° C. over 15 min, using PCR thermocycler.
2) Irradiated for 20 min at 4° C., in Eppendorf UVette plastic cuvette, covered top with parafilm, laid on the top of UV lamp (1 mW/cm² multi-wavelength UV lamp (λ>300 nm) (UV L21 model λ 365 nm).

Steps 1 and 2 above were repeated 4 times to re-intercalate and irradiate HMT. After the second irradiation additional 10 µl of 1.6 mM HMT was added in total 100 µl reaction volume. After 4 cycles of irradiation, the free psoralens were extracted with chloroform and all oligos (labeled and unlabeled) were precipitated with ethanol overnight (see precipitation step). A small aliquot was saved for gel identification.

Step 2: Purification of HMT Conjugated Fragment 2 (2MA) Oligo by HPLC

1) The reaction mixture was dried with speed vacuum for 10 minutes and then was dissolved with 2 µl of 0.1 M TEAA, pH 7.0 buffer.
0.1 M TEAA, pH 7.0 Buffer

| | |
|---|---|
| Acetic Acid | 5.6 ml |
| Triethylamine | 13.86 ml |
| H₂0 (RNAase free) | 950 ml |
| pH adjusted to 7.0 with acetic acid and water added to 1 L | |

2) The sample was loaded onto a Waters Xterra MS C18, 2.5 µm, 4.5×50 mm reverse-phase column pre-equilibrated with buffer A (5% wt/wt acetonitrile in 0.1M TEAA, pH 7.0) The sample was eluted with a gradient of 0-55% buffer B (15% wt/wt acetonitrile in 0.1M TEAA, pH 7.0) to buffer A over a 35 minute time frame at a flow rate of 1 ml/minute. The column temperature was 60° C. and the detection wave length, set by a narrow band filter, was 340 nm. Furan sided psoralen monoadduct absorbs at 340 nm but the RNA, and any pyrone sided monoadduct does not. The buffer solutions were filtered and degassed before use.

The 2MA eluted at around 25-28 minutes at a buffer B concentration of 40%. Unpsoralenated fragment 2 eluted before 8 minutes based on subsequent gel electrophoresis analysis on collected fractions.

The column was washed with 100% acetonitrile for 5 minutes and was re-equilibrated with buffer A for 15 minutes. All fractions were dried with speed vacuum overnight.

The fractions containing the 2MA were identified by the level of absorbance at 260 nm (RNA) and 330 nm (furan sided psoralen monoadducted RNA). This was done by redissolving the dried fractions with 120 µl of Rnase-free distilled water and the absorbance was measured with a spectrophotometer at 260 nm and 330 nm. The fractions with high absorbance at both wavelengths were pooled then dried with speed vacuum. A small aliquot from each was saved for gel analysis.

The cross-linked products were analyzed on a denaturing 20% TBE-urea gel and visualized by gel silver staining.

Step 3: Purification of HMT Conjugated Fragment 2 Oligo from cRNA by HPLC

The dried samples were pooled and then were dissolved with 0.5×TE buffer. A sample of about 0.4 absorbance unit was loaded onto a Dionex DNAPac PA-100 (4×250 mm) column which was pre-equilibrated with buffer C (25 mM Tris-HCl, pH 8.0) and the column temperature was 85° C. (anion exchange HPLC).

The oligos were eluted at a flow rate of 1 ml/min. with a concave gradient from 4% to 55% buffer D for 15 minutes followed by a convex gradient from 55% to 80% with buffer D for the next 15 minutes. The oligos were washed with 100% buffer D for 5 min and 100% buffer C for another 5 min at a flow rate of 1.5 ml/min; Fractions were collected that absorbed 260 nm light. 2MA had a retention time (RT) of 16.2 minutes and was eluted by 57% buffer D, and free fragment 2 had RT less than 16.6 minutes, and was eluted by 55% buffer D and free cRNA had RT greater than 19.2 minutes. The fractions were collected that absorbed at 254 or 260 nm. The collected fractions were dried with speed vacuum overnight. All solutions were filtered and degassed before use.

The solution used comprised the following:
C: 25 mM Tris-HCl pH 8.0;
D: 250 mM NaClO4 in 25 mM Tris pH 8.0 buffer.
TE: 10 mM Tris-HCl pH 8.0 with 1 mM EDTA Step 4: Desalting, Precipitation and Collection of the Purified 2MA Oligo The dried fractions were redissolved with 100 µl Rnase free distilled water. 500 µl cool 100% ethanol with 0.5M (NH4)2CO3 was added and the mixture was vortexed briefly. The mixture was then frozen on dry ice for 60 minutes or stored at −20° C. overnight.

The samples were then brought to 4° C. and centrifuged at maximum speed in a microcentrifuge for 15 minutes. The position of the pellet was noted and the supernatant was decanted or removed by pipette. Care was taken not to disturb pellet. If the pellet still contained salt, this step was repeated. The pellet was then washed with 70% pre-cooled ethanol twice. The wet pellet was dried with speed vacuum for 15 min. Urea PAGE gel identified the right fractions for the next step.

Step 5: Ligation of 2MA Oligo to Fragment 3 Oligo

The following steps were performed:
A. The Following Reagents and Instruments were Used:
Nuclease-Free Water (Promega)
polyethylene glycol (PEG8000 Sigma) 40% (wt/wt in water)
RNasin® Ribonuclease Inhibitor (Promega)
phenol:chloroform
1.5 ml sterile microcentrifuge tubes
100% ethanol
70% ethanol
Dry ice or −20° C. freezer
Microcentrifuge at room temperature and +4° C.
PCR thermocycler or water bath
B. The Following Reaction Conditions were Used:
50 mM Tris-HCl (pH 7.8)
10 mM MgCl2,
10 mM DTT
1 mM ATP
18-20% PEG
C. The Following Reaction Mixture was Assembled in a Sterile Microcentrifuge Tube:

Fragment 3 (Donor) 1 µl (6 µg) (Purified, when necessary, before using as a donor)
2MA (Acceptor) 1 µl (1.5 µg)

After adding 8 µl Rnase free dH2O 8 µl, the reactions were incubated at 85° C. for 1 minute to relax the oligo secondary structure, then slowly cooled to 4° C., using a PCR machine thermocycler. The preheated tube was placed on ice to keep cool and centrifuged briefly, then the following was added:

| 10X Ligase Buffer | 4 µl |
| 10 mM ATP | 4 µl |
| Rnase Out or Rnasin(40 u/µl) Promega | 0.5 µl |
| PEG, 40% (Sigma) | 20 µl |
| T4 RNA Ligase (10 u/µl) (NEB) | 1 µl |

Nuclease-free water was added to final Volume of 40 µl. The mixture was incubate at 16° C. overnight (16 hr). The mixture was centrifuged briefly and then was placed on ice.

D. Precipitation of Oligonucleotides:

60 µl DEPC RNase free distilled water was added to the mixture and then 150 µl phenol/chloroform was added. The mixture was vortexed vigorously for 30 seconds. The precipitate was then centrifuged out at maximum speed in a microcentrifuge for 5 minutes at room temperature. The aqueous phase was transferred to a new microcentrifuge tube (>95 µl).

To this was added 3 µl 15 mg/ml glycogen, and 500 µl pre-cooled 100% ethanol with 0.5M (NH4)2CO3 and the mixture was vortexed briefly and then was frozen on dry ice for 60 minutes. At this point, it may be stored overnight at −20° C. The dried fractions were redissolved with 100 µl Rnase-free distilled water, 500 µl cool 100% ethanol with 0.5M (NH4)2CO3 was added and vortexed briefly. This was then frozen on dry ice for 60 minutes or stored at −20 C overnight. The samples were then brought to 4° C. and centrifuged at maximum speed in a microcentrifuge for 15 minutes and supernatant removed by pipette. Care was taken not to disturb pellet. If the pellet still contained salt, this step was repeated once. The pellet was then washed with 70% pre-cooled ethanol several times. This was then centrifuged at maximum speed in a microcentrifuge for 5 minutes at 4 C. The ethanol was carefully removed using a pipette. Centrifugation was repeated again to collect remaining ethanol which was carefully removed. The wet pellet was dried with speed vacuum for 10 min. A small aliquot was collected for the gel analysis. For long term storage, the RNA was stored in ethanol at −20 C. Care was taken not to store the RNA in DEPC water.

Step 6: Purification of the Ligated Fragment 3 Oligo Complex

The dried sample was redissolved with 0.5×TE buffer and was loaded onto a DNAPac PA-100 column which was equilibrated with buffer C. The column temperature was 85° C. and the detector operated at 254 nm to identify fractions with RNA and at 340 nm to identify fractions with 2MaF. The oligos were eluted with a convex gradient from 30% to 70% with buffer D for the first 20 minutes at a flow rate of 0.8 ml/min and followed with a linear gradient from 70% to 98% D for another 20 min at the same flow rate. The elution was completed by washing with 100% D for 7 min and 100% C for another 10 min at 1.0 ml/min flow rate. The fractions were detected with 254 or 260 nm wavelength light. The ligated oligos (2MA-fragment 3) were eluted after 34 min, by more than 90% buffer B. Fractions with 254 nm absorbance (A254 nm>0.01) were collected and dried with speed vacuum overnight.

Step 7: Purified 2MA-Fragment 3 Desalting and Precipitation

The dried fractions were re-dissolved with 100 μl Rnase free distilled water, 500 μl cool 100% ethanol with 0.5M (NH4)2CO3 was added and the mixture was vortexed briefly. The mixture was then frozen on dry ice for 60 minutes or stored at −20 C overnight.

The samples were brought to 4° C. and centrifuged at maximum speed in a microcentrifuge for 15 minutes. The position of the pellet was noted and the supernatant decanted or removed by pipette. Care was taken not to disturb pellet. If still containing salt, this step was repeated. The pellet was then washed with 70% pre-cooled ethanol twice. The wet pellet was dried with speed vacuum for 15 min.

Urea PAGE was performed to identify the ligated 2MA-fragment-3 for use in the next step of ligating fragment 1 to the 2MA-fragment-3 oligo which completes the SATA linker.

Step 8: Preparation of SATA (or Other tRNA Molecule)

A. RNA Oligo 5' phosphorylation

1. Reagent and Instrument:
   Nuclease-Free Water (Cat.# P1193 Promega)
   RNasin® Ribonuclease Inhibitor (Cat# N2511 Promega)
   Phenol:chloroform
   Sterile microcentrifuge tubes
   100% ethanol
   70% ethanol
   Microcentrifuge at room temperature and 4° C.
   PCR thermalcycler or water bath 2. Assemble the Following Reaction Mixture in a Sterile Microcentrifuge Tube:

| Component | Volume |
|---|---|
| Acceptor RNA | <200 ng |
| T4 ligase 10X Reaction Buffer* | 4 μl |
| RNasin ® Ribonuclease Inhibitor (40 u/μl) | 20 unit |
| T4 kinase (9-12 u/μl) | 2 μl |
| 10 mM ATP | 4 μl |
| Nuclease-Free Water to final volume | 40 μl |

Incubate at 37° C. for 30 minutes in a PCR thermocycler or water bath. For non-radioactive phosphorylation, use up to 300 pmol of 5' termini in a 30 to 40 μl reaction containing 1×T4 Polynucleotide Kinase Reaction Buffer, 1 mM ATP and 10 to 20 units of T4 Polynucleotide Kinase. Incubate at 37° C. for 30 minutes. 1×T4 DNA Ligase Reaction Buffer contains 1 mM ATP and can be substituted in non-radioactive phosphorylations. T4 Polynucleotide Kinase exhibits 100% activity in this buffer). Fresh buffer is required for optimal activity (in older buffers, loss of DTT due to oxidation lowers activity.

B. Annealing Fragment 1 and 2MA-Fragment 3 Oligo Complex:

1. Reagents and Instruments:
   PCR thermocycler instrument or water bath
   100 μg/ml nuclease-free albumin
   100 mM MgCl2

2. Assemble the Following Reaction Mixture in a Sterile Microcentrifuge Tube:

| | |
|---|---|
| Acceptor RNA oligo (1E) | <200 ng |
| Donor RNA oligo (3G-2G ligated oligo) (5' phosphorylated oligo from step A) | <200 ng |

Appropriate ratios are as follows: Acceptor oligo:Donor oligo (Fragment 1:2MA-Fragment 3) molar ratio should be 1:1.1 to avoid fragment 1 self-ligation. MgCl$_2$ was added to T4 ligase buffer (50 mM Tris-HCL, pH 7.8, 10 mM MgCl$_2$, 10 mM DTT and 1 mM ATP) to final 20 mM concentration. Add Rnase free albumin to final 5 μg/ml. The final volume should be no more than 100 μl. The solution was heated to 70° C. for 5 min, then was cooled from 70° C. to 26° C. over 2 hours and cooled from 26° C. to 0° C. over 40 minutes. Incubate at 16° C. for 16 to 17 hours using PCR instrument.

C. Ligation Of Annealed Oligos

| | |
|---|---|
| Annealed oligos | <15 μl |
| 10 mM ATP | 2 μl |
| 40% PEG | 18 μl |
| T4 ligase 10X Buffer | 2 μl |
| RNasin ® Ribonuclease Inhibitor (40 u/μl) | 0.5 μl |
| T4 ligase (9-12 u/μl)(NEB) | 1 μl |
| Nuclease-Free Water to final volume | 40 μl |

D. Precipitating tRNA Fragment

After ligation, 50 μl DEPC water and 150 μl phenol: chloroform were added and vortexed vigorously for 30 seconds. This was then centrifuged at maximum speed in a microcentrifuge for 5 minutes at room temperature. The aqueous phase was transferred to a new microcentrifuge tube (~100 μl). To this was added 2 μl 10 mg/ml mussel glycogen, 10 μl 3M sodium acetate, pH 5.2. This was mixed well. Then 220 μl 95% ethanol was added and vortexed briefly. The mixture was then frozen on dry ice for 30 minutes. At this point the mixture may be stored over night at −20° C. or one may proceed. In one embodiment, the RNA should preferably not be stored in DEPC water, but in ethanol, at −20° C.

Then the samples were brought to 4° C. and centrifuged at maximum speed in a microcentrifuge for 15 minutes. The position of the pellet was noted and the supernatant decanted or removed by pipette. Care was taken not to disturb pellet. The pellet was then washed with 70% pre-cooled ethanol twice. After removing the ethanol, the wet pellet was dried with a speed vacuum for 15 min. The dried pellet was stored −20° C., until the next step.

RNA Translation

A luciferase mRNA which was modified to have the stop codon corresponding to that recognized by the anticodon of the SATA (in the present case UAG) was used in a standard Promega in vitro translation kit in the recommended 1 μl of concentration 1 μg/μl. One skilled in the art will understand that indeed any mRNA fragment containing the appropriate sequences may be used.

SATA was added to the experimental tubes. Control tubes which did not contain SATA were also prepared. The quantity of SATA used was approximately between 0.1 μg to 500 μg, preferably between 0.5 μg to 50 μg. 1 μl of at 40 units/ml was added. Nuclease free water was added to make a total volume of 50 μl.

For proteins greater than approximately 150 amino acids, the amount of tRNA may need to be supplemented. For example, approximately 10-200 μg of tRNA may be added. In general, the quantity of the SATA should be high enough to effectively suppress stop or pseudo stop codons. The quantity of the native tRNA must be high enough to out compete the SATA which does not undergo dynamic proofreading under the action of elongation factors.

Each tube was immediately capped, parafilmed and incubated for the translation reactions at 30° C. for 90 minutes. The contents of each reaction tube was transferred into a 50 μl quartz capillary tube by capillary action. The SATA was crosslinked with mRNA by illuminating the contents of each tube with 2-10 J/cm2~350 nm wavelength light, as per Gasparro et al. (Photochem. Photobiol. 57:1007 (1993), herein incorporated by reference). Following photocrosslinking, the contents of each tube were transferred into a new snapcap microfuge tube. The ribosomes were dissociated by chelating the calcium cations by adding 2 μl of 10 mM EDTA to each tube. Between each step, each tube was gently mixed by stirring each component with a pipette tip upon addition.

The optimal RNA for a translation was determined prior to performing definitive experiments. Serial dilutions may be required to find the optimal concentration of mRNA between 5-20 μg/ml.

SDS-Page electrophoresis was performed on each sample, as described above. Autoradiography on the gel was performed, as described by Sambrook et al., Molecular Cloning, A Laboratory Manual, 2$^{nd}$ ed., Coldspring Harbor Press (1989), herein incorporated by reference.

The above example is instructive for the production and use of SATA (puromycin on tRNA and crosslinker on tRNA) and for the production and use of Linking tRNA Analog (no puromycin, with crosslinker on tRNA).

Example 4

Production of a tRNA Analog Using Ribonucleotides Modified to Form Crosslinkers: Use of Psoralen and Non-Psoralen Cross-Linkers As described above, pseudouridine can be used in some embodiments to minimize the formation of unwanted monoadducts and crosslinks. In one embodiment, a crosslinker modified mononucleotide is formed and used. One advantage of the crosslinker modified mononucleotide is that it minimizes the formation of undesirable monoadducts and crosslinks.

As discussed above, one skilled in the art will appreciate that the SATA, Linking tRNA Analog, and Nonsense Suppressor Analog can be produced in a number of different ways. In a preferred embodiment, psoralenated uridine 5' mononucleotide, 2-thiocytosine, 2-thiouridine, 4-thiouridine 5-iodocytosine, 5-iodouridine, 5-bromouridine or 2-chloroadenosine can be produced or purchased and enzymatically ligated to an oligonucleotide to be incorporated into a tRNA analog. Aryl azides, and analogues of aryl azides, and any modifications thereto, can also be used in several embodiments, as a linking moiety or agent. The following protocol can be employed for crosslinkers that are located on the tRNA. One skilled in the art will understand that this protocol can also be used for crosslinkers located on the mRNA. Thus, the following example is instructive on the production and use of SATA, Linking tRNA Analog, and Nonsense Suppressor Analog.

Production of Modified Nucleotide 4-thioU, 5-iodo and 5-bromo U with and without puromycin can be purchased already incorporated into a custom nucleotide up to 80 basepairs in length (Dharmacon, Inc). Therefore, the SATA, and the Linking tRNA Analog with these crosslinkers already in place, and similar crosslinkers, can be purchased directly from Dharmacon, Inc. Nonsense Suppressor Analog can also be purchased from Dharmacon, Inc.

2-thiocytosine, 2-thiouridine, 4thiouridine 5-iodocytosine, 5-iodouridine, 5-bromouridine or 2-chloroadenosine can all be purchased for crosslinking from Ambion, Inc. for the use in the Ambion MODIscript kit for incorporation into RNA. Therefore, the SATA and the Linking tRNA Analog along with these crosslinkers, and similar crosslinkers, can be purchased directly from Ambion, Inc The PO$_4$U$_{psoralen}$ can be produced as follows:

```
                                          (SEQ ID NO: 20)
AUAUAUAUAUAUAUAUAUAUAUGGGGGG  (seq A1) (available from Dharmacon, Inc.)

(SEQ ID NO: 21)
CCCCCCATATATATATATATATATAT    (seq A2) (available from University of Southern California services).
```

The formation of a furan-sided psoralen monoadduct with the target uridine is performed as follows:

A reaction buffer is prepared. The reaction buffer, with a pH of 7.0, contains 25 mM Tris HCL, 100 mM NaCl, and 0.32 mM EDTA.

4'hydroxy methyl-4,5',8'-triethyl psoralen (HMT) is then added to a final concentration of 0.32 mM and equimolar amounts of seq A1 and seq A2 are added to a final molar ratio of seq A1:seq A2:psoralen=1:1:1000. A total volume of 100 μl is irradiated at a time.

The mixture of complementary oligos, HMT, trimethylpsoralen is processed as follows: 1) Heat to 85° C. for 60 sec followed by cooling to 4° C. over 15 min, using PCR thermocycler; and 2) Irradiate for 20 to 60 min at 4° C., in Eppendorf UVette plastic cuvette, covered top with parafilm, in an RPR-200 Rayonet Chamber Reactor equipped with a cooling fan and 419 nm wave. This is either placed on an ice water bath or in a −20° C. freezer.

Steps 1 and 2 above are repeated 4 times to re-intercalate and irradiate HMT. After 4 cycles of irradiation, the free psoralens are extracted with chloroform and all oligos (labeled and unlabeled) are precipitated with ethanol overnight (see precipitation step). A small aliquot is saved for gel identification.

Comparable sequences can be produced using the Ambion, Inc kit for non-psoralen crosslinkers.

RNase H Digestion of RNAs in DNA/RNA Duplexes

The following steps are performed: (1) Dry down oligos in speed vac; (2) Resuspend pellet in 10 μL 1×Hyb Mix; (3) Heat at 68° C. for 10 minutes; (4) Cool slowly to 30° C. Pulse spin down; (5) Add 10 μL 2×RNase H Buffer. Mix. (6) Incubate at 30° C. for 60 minutes; (7) Add 13 μL Stop Mix.

For the Phenol/Chloroform extract: (1) Add 1 vol. phenol/chloroform; (2) Vortex well; (3) Spin down 2 minutes in room temperature microfuge; (4) Remove top layer to new tube.

For the Chloroform extract: (1) Add 1 vol. chloroform; (2) Vortex well; (3) Spin down 2 minutes in room temperature microfuge; (4) Remove top layer to new tube.

Then, (1) Add 375 μL 100% ethanol; (2) Freeze at −80° C.; (3) Spin down 10 minutes in room temperature microfuge; (4) Wash pellet with 70% ethanol; (5) Resuspend in 10 μL loading dye; (6) Heat at 100° C. for 3 minutes immediately before loading.

Purification of monoribonucleotides nucleotides from the longer cDNA as well as longer RNA fragments, is accomplished using anion exchange HPLC. The psoralen-monoadducted mononucleotides (PO$_4$U$_{psoralen}$) are then separated by reverse phase HPLC from mononucleotides that were not monoadducted (PO$_4$U and PO$_4$A).

Similar digestion techniques and nucleotide incorporation, described below, can also be used for non-psoralen crosslinkers using the Ambion, Inc kit.

Incorporation of Light Sensitive Nucleotides into the tRNA Component Oligoribonucleotides The following protocol can be used for incorporating a $pU_{crosslinker}$ into a CUA stop anticodon. However, one skilled in the art will understand that other nucleotides can also be used to produce other stop anticodons and pseudo stop anticodons in accordance with the methods described herein Generally, methods adapted from the protocols for T4 RNA ligase are used, but with some modification because of the lack of protection of the 3' OH of the modified nucleotides.

5'OH CUC OH 3' oligoribonucleotides (seq B1) can be purchased from Dharmacon, Inc. and can be as acceptors in the ligation. The molar ratio of B1 to psoralenated mononucleotides is preferably kept at 10:1 to 50:1 so that the modified U's will be greatly out-numbered, thereby preventing the formation of $CUC(U_{crosslinker})_N$. This makes one of the preferred reactions:

$CUC + pU_{psoralen} \rightarrow CUCU_{psoralen}$

In one embodiment, the product is purified by sequential anion exchange and reversed phase HPLC to ensure that the psoralenated U and the longer psoralenated 7 mer are separated. The 7 mer is then 3' protected by ligation with pAp yielding $CUCU_{crosslinker}Ap$ (Fragment 2B).

This is again purified with anion exchange HPLCF or the next ligation.

First Ligation of Fragment 2B to 1B or 1B1

This 2B fragment can be used in a tRNA analog that has a stable acceptor or one that has a native esterified acceptor. In one embodiment, to assure that the native 3' end can be aminoacylated by native AA-tRNA synthetases, the acceptor stem is modified in that version of the analog. In the SATA version, in one embodiment, the 3' fragment is maintained with a commercially prepared puromycin as the acceptor. Thus, in one embodiment, the following are used in two different 5' ends:

5' OHGCGGAUUUAGCUCAGUUGGGAGAGCGCCAGA 3' seq 1B (SEQ ID NO: 22)

(to be used with the tRNA analog with the stable puromycin acceptor)

and

5' OHGGGGCUUUAGCUCAGUUGGGAGAGCGCCAGA 3' seq $1B_1$ (SEQ ID NO: 23)

(to be used with the native esterified acceptor).

The ligation is performed again with T4 RNA ligase and purified by length. The equation for sequence 1B is as follows:

5' OHGCGGAUUUAGCUCAGUUGGGAGAGCGCCAGA 3' + $CUCU_{crosslinker}APO_4$ 3'  (SEQ ID NO: 22)

5' OHGCGGAUUUAGCUCAGUUGGGAGAGCGCCAGACUCU$_{crosslinker}$APO$_4$ 3'  (SEQ ID NO: 24)

For sequence $1B_1$:

5' OHGGGGCUUUAGCUCAGUUGGGAGAGCGCCAGA + $CUCU_{crosslinker}APO_4$ 3'  (SEQ ID NO: 23)

→

5' OHGGGGCUUUAGCUCAGUUGGGAGAGCGCCAGACUCU$_{crosslinker}$APO$_4$ 3'  (SEQ ID NO: 25)

Ligation of the Two Half-Molecules of the TRNA Analog

The above product is treated with T4 polynucleotide kinase in two separate steps to remove the 3' phosphate and add a 5' phosphate.

The newly prepared 5' and 3' half molecules ends are then ligated generally following the previous protocols. The 3' sequences corresponding to the respective 5' sequences are as follows:

Sequence 1B: (Ψ = pseudouridine)
5' PO$_4$GCGGAUUUAGCUCAGUUGGGAGAGCGCCAGACUCU$_{crosslinker}$A 3'  (SEQ ID NO: 24)

corresponded to the 3' half:
5'PO$_4$UGGAGGUCCUGUGTΨCGAUCCACAGAAUUCGCACCPur 3', 3B  (SEQ ID NO: 31)
and sequence 1B1,
5' OHGGGGCUUUAGCUCAGUUGGGAGAGCGCCAGACUCU$_{crosslinker}$APO$_4$  (SEQ ID NO: 25)

corresponded to 3' half
5'PO$_4$UGGAGGUCCUGUGTΨCGAUCCACAGAAUCUCCACCA3'.  (SEQ ID NO: 32)

The latter is recognizable by the aminoacyl tRNA synthetase for alanine in *E. coli*.

The example described above can be used to make and use the SATA, Linking tRNA, and the Nonsense Suppressor tRNA.

Example 5

Placement of Crosslinkers on the mRNA for Sata and Nonsense Suppressor tRNA

In several embodiments, the crosslinker (such as psoralen or a non-psoralen crosslinker) is not placed on the tRNA, but rather located on the mRNA. For example, in one embodiment, the SATA comprises a puromycin located on the tRNA, while the crosslinker is on the mRNA. In yet another embodiment, the Nonsense Suppressor tRNA is used, and this comprises a tRNA with no puromycin, with the crosslinker being on the mRNA. Placement of the crosslinker on the message (the mRNA) can be accomplished as set forth below. The relevant sequence is as follows:

```
                                            (SEQ ID NO: 26)
GGGUUAACUUUAGAAGGAGGUCGCCACCAUG GUU AAA AUG AAA

AUG AAA AUG AAA AUG U_crosslinker AG
```

For convenience only, and in one embodiment, a message with both Kozak and Shine Dalgarno sequences that has a large number of methionine codons for $^{35}$S labeling is used.

For 4-thiouridine, 5-bromouridine and 5-iodouridine, the message can be purchased fully-made from Dharmacon, Inc. For aryl azides, the method recited in Demeshkina, N, et al., RNA 6:1727-1736, 2000, herein incorporated by reference, can be used.

For 2-thiocytosine, 2-thiouridine, 5-iodocytosine, or 2-chloroadenosine, the modified bases can be purchased as the 5' monophosphate nucleotide from Ambion, Inc. When psoralen is used as the crosslinker, the modified 5' monophosphate nucleotide is made as above.

The modified 5' monophosphate nucleotides are first incorporated into hexamers to facilitate purification. The construction of uridine containing crosslinkers is shown but in several embodiments, the other bases can be incorporated into both stop and pseudo stop codons using similar techniques:

AUG+pUcrosslinker→AUGUcrosslinker was accomplished using a similar protocol described above, except a preponderance of AUG was used because of the absence of a 3' protection of the pNcrosslinker. The product was purified by anion exchange HPLC from the excess of AUG. Then 5' pAGbiotin 3' was added with T4 RNA ligase. The 3' biotin was simply a convenient 3' blocking group available form Dharmacon. The resulting AUGU$_{crosslinker}$AG$_{biotin}$ was again purified followed by 5' phosphorylation and ligated to:

```
                                            (SEQ ID NO: 27)
GGGUUAACUUUAGAAGGAGGUCGCCACCAUGGUUAAAAUGAAAAUGAA

AAUGAAA (sequence M1)

to produce
                                            (SEQ ID NO: 28)
GGGUUAACUUUAGAAGGAGGUCGCCACCAUGGNNAAAAUGAAAAUG AAAAUGAAAAUGU_crosslinker AG_biotin.
```

The yield is high enough to obviate purification. Accordingly, using the protocol described above, SATAs and Nonsense Suppressor tRNAs can be made and used in accordance with several embodiments of the present invention.

Example 6

Using tRNA Systems that do not Require Puromycin

Several embodiments of the present invention provide a system and method that do not require puromycin, puromycin analogs, or other amide linkers. In one embodiment, Linking tRNA Analogs and Nonsense Suppressor tRNAs do not require puromycin and can be made and used according to the following example.

For systems without puromycin, a translation system to aminoacylate the tRNA can be used. In other embodiments, aminoacylation can be accomplished chemically. One skilled in the art will understand how to chemically aminoacylate tRNA. Where translation systems are used, any type of translation system for aminoacylation can be employed, such as in vitro, in vivo and in situ. In one embodiment, am e-coli translation system is used. An *E. coli* translation system is used for systems with a tRNA modified to be recognized by the aaRS$^{Ala}$. In one embodiment, this is preferable for systems without the stable acceptor (e.g. the puromycin)

3 mcg of each of the following mRNA's are translated in 40 microliters each of Promega S30 *E. coli* translation mixture:

```
                                            (SEQ ID NO: 28)
a)  GGGUUAACUUUAGAAGGAGGUCGCCACCAUG GUU AAA AUG AAA

AUG AAA AUG AAA AUGUcrosslinkerAGbiotin
and
                                            (SEQ ID NO: 29)
b)  GGGUUAACUUUAGAAGGAGGUCGCCACCAUG GUU AAA AUG AAA

AUG AAA AUG AAA AUGUAG
```

3 mcg of amber suppressor tRNA manufactured as above are added to the first. 3 mcg of suppressor with crosslinker on the anticodon are added to the second. 35S-methionine is added to both and the mixtures are then incubated at 37° C. for 30 minutes. The reactions are then rapidly cooled by placement in an ice bath, transferred to a flat Petri dish and floated in an ice bath so that the mixture is 1.5 cm below a ~350 nm light source. They are exposed at ~20 J/cm for 15 min.

After irradiation, the mixtures are phenol extracted and ethanol precipitated. In this manner, systems such as the Linking tRNA Analogs and Nonsense Suppressor tRNAs are aminoacylated and used to connect the message (mRNA) to its coded peptide in accordance with several embodiments of the present invention.

Example 7

Alternative Sequences

In a preferred embodiment, Fragments 1, 2 and 3, described above in Example 1, have the following alternate sequences:

```
Fragment 1 (SEQ ID NO: 13):
5' PO4 GCGGAUUUAGCUCAGUUGGGAGAGCGCCAGA N3-Methyl-

U 3'

Fragment 2 (SEQ ID NO: 14):
5' UCUAAGΨCΨGGAGG 3'
```

-continued

Fragment 3-Unchanged from the sequence listed
above (SEQ ID NO: 6):
5' PO4 UCCUGUGTΨCGAUCCACAGAAUUCGCACC Puromycin 3'

Using the methods described above, the sequence of alternative Fragments 1+2+3 was (SEQ ID NO: 15):

5'PO4GCGGAUUUAGCUCAGUUGGGAGAGCGCCAGA(N3-Methy1U)

UCUPsoralenAAGΨCΨGGAGGUCCUGUGTYCGAUCCACAGAAUUC

GPuromycin 3'

For linking tRNA Analog and Nonsense Suppressor tRNA, the above sequences are similar, except adenosine is used to replace puromycin.

While a number of preferred embodiments of the current invention and variations thereof have been described in detail, other modifications and methods of use will be readily apparent to those of skill in the art. For all of the embodiments described above, the steps of the methods need not be performed sequentially. Accordingly, it should be understood that various applications, modifications and substitutions may be made without departing from the spirit of the invention or the scope of the claims.

What is claimed is:

1. A composition comprising a targeted therapeutic agent, said agent comprising:
   a first non-antibody protein portion that selectively or preferentially binds to a marker expressed on a surface of diseased cells,
   a non-antibody second portion other than complement that binds to a portion of the constant region of an antibody to a degree sufficient to induce an immune response against said diseased cells expressing said marker; and
   a linker that links said first non-antibody protein portion and second non-antibody portion without interfering with the selective or preferential binding of the first non-antibody protein portion with the marker or the binding of the second non-antibody portion with the portion of the constant region of an antibody.

2. The composition of claim 1, wherein the diseased cells are cancerous cells.

3. The composition of claim 2, wherein the cancerous cells B-cells comprise B-cells of a solid tumor.

4. The composition of claim 3, wherein said surface marker is a cancer B-cell-specific epitope that is mutated in said subject.

5. The composition of claim 1, wherein the diseased cells are a result of hematological cancer.

6. The composition of claim 1, wherein the first non-antibody protein portion, the linker and the non-antibody second portion together form a fusion protein.

7. The composition of claim 1, wherein said linker comprises a polypeptide.

* * * * *